(12) United States Patent
Goldstein

(10) Patent No.: US 7,943,140 B2
(45) Date of Patent: May 17, 2011

(54) COMPOSITIONS AND METHODS FOR THE TREATMENT AND PROPHYLAXIS OF MULTIPLE STRAINS AND SUBTYPES OF HIV-1

(75) Inventor: Gideon Goldstein, Short Hills, NJ (US)

(73) Assignee: Thymon, LLC, Short Hills, NJ (US)

( * ) Notice: Subject to any disclaimer, the term of this patent is extended or adjusted under 35 U.S.C. 154(b) by 508 days.

(21) Appl. No.: 11/891,893

(22) Filed: Aug. 14, 2007

(65) Prior Publication Data

US 2009/0092626 A1    Apr. 9, 2009

Related U.S. Application Data

(60) Provisional application No. 60/837,493, filed on Aug. 14, 2006.

(51) Int. Cl.
*A61K 39/00* (2006.01)
*C12N 7/00* (2006.01)

(52) U.S. Cl. ............... 424/188.1; 424/204.1; 435/235.1

(58) Field of Classification Search .................. None
See application file for complete search history.

(56) References Cited

U.S. PATENT DOCUMENTS

| | | | |
|---|---|---|---|
| 5,891,994 A | 4/1999 | Goldstein | |
| 6,193,981 B1 | 2/2001 | Goldstein | |
| 6,399,067 B1 | 6/2002 | Goldstein | |
| 6,524,582 B2 | 2/2003 | Goldstein | |
| 6,525,179 B1 | 2/2003 | Goldstein | |
| 7,008,622 B2 | 3/2006 | Goldstein | |
| 7,569,225 B2 * | 8/2009 | Jackson et al. ............ | 424/184.1 |
| 2005/0032114 A1 | 2/2005 | Hinton et al. | |
| 2005/0036985 A1 | 2/2005 | Ensoli | |
| 2006/0078554 A1 | 4/2006 | Bachman et al. | |

FOREIGN PATENT DOCUMENTS

| WO | WO 93/03764 | * 3/1993 |
|---|---|---|
| WO | WO 99/02185 | * 1/1999 |
| WO | WO 99/27958 | 6/1999 |
| WO | WO 00/78969 | * 12/2000 |
| WO | WO 01/82944 | 11/2001 |
| WO | WO 03/009867 | 2/2003 |
| WO | WO2004/014956 | 2/2004 |
| WO | WO 2004/014957 | 2/2004 |
| WO | WO 2004/056316 | 7/2004 |
| WO | WO 2005/039631 | 5/2005 |
| WO | WO 2005/090391 | 9/2005 |
| WO | 2007/146070 | 12/2007 |
| WO | WO2008/021296 | 2/2008 |
| WO | WO2009/023714 | 2/2009 |

OTHER PUBLICATIONS

Kumar, Enhancing immunogenicity of HIV-1 PND by using foreign T-h epitope, Int Conf AIDS, Aug. 7-12, 1994; 10: 119 (abstract No. PA0356).*
deMan, Principles of Food Chemistry, 1999, Aspen Publishers, Inc.*
G. Goldstein, "HIV-1 Tat protein as a potential AIDS vaccine", Nat. Med., 2(9):960-964 (Sep. 1996).
G. Goldstein, "Minimization of chronic plasma viremia in rhesus macaques immunized with synthetic HIV-1 Tat peptides and infected with a chimeric simian/human immunodeficiency virus (SHIV33)", Vaccine, 18(25):2789-2795 (Jun. 15, 2000).
Hoffmann, et al., "Stimulation of human and murine adherent cells by bacterial lipoprotein and synthetic lipopeptide analogues", Immunobiology, 177(2):158-170 (May 1988).
Buwitt-Beckmann, et al., "Toll-like receptor 6-independent signaling by diacylated lipopeptides", Eur. J. Immuno. , 35(1):282-289 (Jan. 2005).
Vitiello, et al., "Development of a lipopeptide-based therapeutic vaccine to treat chronic HBV infection. I. Induction of a primary cytotoxic T lymphocyte response in humans", J. Clin. Invest., 95(1):341-349 (Jan. 1995).
Mühlradt, et al., "Isolation, structure elucidation, and synthesis of a macrophage stimulatory lipopeptide from *Mycoplasma fermentans* acting at picomolar concentration", J. Exp. Med., 185(11):1951-1958 (Jun. 2, 1997).
Zeng, et al., "Highly immunogenic and totally synthetic lipopeptides as self-adjuvanting immunocontraceptive vaccines", J. Immunol., 169(9):4905-4912 (Nov. 1, 2002).
Jackson, et al., "A totally synthetic vaccine of generic structure that targets Toll-like receptor 2 on dendritic cells and promotes antibody or cytotoxic T cell responses", Proc. Natl. Acad. Sci. USA, 101(43):15440-15445 (Oct. 26, 2004 ; E-pub Oct. 15, 2004).

(Continued)

*Primary Examiner* — Stacy B Chen
*Assistant Examiner* — Nicole Kinsey White
(74) *Attorney, Agent, or Firm* — Howson & Howson LLP

(57) ABSTRACT

A self-adjuvanting immunogenic composition comprising multiple immunogens, each immunogen comprising a lipopeptide cap, a universal T helper sequence and an immunodominant HIV-1 Tat B cell epitope. The immunogen also comprises one or more linker sequences and/or polar charged amino acid sequences. The HIV-1 Tat B cell epitope of each immunogen has an amino acid sequence of V-D-P-Xaa7-L-Xaa9-P-W-Xaa12-Xaa13-Xaa14-Xaa15-Xaa16-amide SEQ ID NO: 1, in which the amino acid positions at Xaa7, Xaa9 and Xaa12 are selected from specific amino acid residues choices and in which the amino acid positions at Xaa13-Xaa16 may be absent or specific amino acid residue choices. The lipopeptide is a dipalmitoyl-S-glyceryl-cysteine or a tripalmitoyl-S-glyceryl cysteine or N-acetyl (dipalmitoyl-S-glyceryl cysteine), each with an optional neutral amino acid linker. Optional polar sequences of at least four charged polar amino acids enhance solubility of the immunogen and are located at the carboxy terminal end of the lipopeptide cap, optionally flanked by neutral linker amino acids, or elsewhere in the immunogen. In the composition, each immunogen differs from another immunogen by an amino acid variation at amino acid position Xaa7, Xaa9 or Xaa12 of the immunodominant HIV-1 Tat epitope. Such compositions can induce anti-HIV-1 Tat antibodies with geometric mean titers of greater than 1,000,000 on multiple HIV-1 Tat variants, when employed to immunize a subject, without any extrinsic adjuvant.

16 Claims, 8 Drawing Sheets

OTHER PUBLICATIONS

Livingston, et al., "Altered helper T lymphocyte function associated with chronic hepatitis B virus infection and its role in response to therapeutic vaccination in humans", J. Immunol., 162(5):3088-3095 (Mar. 1, 1999).

Ruckwardt, et al., "Sequence variation within the dominant amino terminus epitope affects antibody binding and neutralization of human immunodeficiency virus type 1 Tat protein", J. Virol., 78(23):13190-13196 (Dec. 2004).

Tikhonov, et al., "Tat-neutralizing antibodies in vaccinated macaques", J. Virol., 77(5):3157-3166 (Mar. 2003).

Goldstein, G. and Chicca, J.J., A universal anti-HIV-1 Tat epitope vaccine that is fully synthetic and self-adjuvanting. Vaccine, Dec. 1, 2009, pp. 1008-1014, vol. 28.

International Preliminary Report on Patentability for co-pending PCT/US2008/07320 by Goldstein.

International Preliminary Report on Patentability for co-pending PCT/US2007/017875 by Goldstein.

International Search Report and Written Opinion for co-pending PCT/US2007/17875 by Goldstein.

Office Action dated Mar. 17, 2010 in co-pending U.S. Appl. No. 11/891,880 by Goldstein.

Amendment in response to Office Action dated Jul. 9, 2009 in co-pending U.S. Appl. No. 11/891,880 by Goldstein.

Boykins et al, Immunization with a novel HIV-1-Tat multiple-peptide conjugate induces effective immune response in mice, Peptides, 21(12): pp. 1839-1847 (Dec. 1, 2000).

Caputo et al, Recent Advances in the Development of HIV-1 Tat-Based Vaccines, Current HIV Research, 2(4):357-376 (Jan. 1, 2004).

Goldstein, Two B cell epitopes of HIV-1 Tat protein have limited antigenic polymorphism in geographically diverse HIV-1 strains, Vaccine, 19(13-14):1738-1746 (Feb. 8, 2001).

Takeda et al, Toll-like Receptors, Annual Review of Immunology, 21:335-376 (Jan. 1, 2003).

Zhu et al, Lipopeptide epitopes extended by an N-epsilon-palmitoyl-lysine moiety increase uptake and maturation of dendritic cells through a toll-like receptor-2 pathway and trigger a Th1-dependent protective immunity, European Journal of Immunology, (11):3102-3114 (Nov. 2004).

European Search Opinion dated Jul. 15, 2010 from corresponding EP Application No. 07836746.3.

* cited by examiner

COMPOSITIONS AND METHODS FOR THE TREATMENT AND PROPHYLAXIS OF MULTIPLE STRAINS AND SUBTYPES OF HIV-1

CROSS-REFERENCE TO RELATED APPLICATIONS

This application claims the benefit under 35 USC 119(e) of prior U.S. Provisional Patent Application No. 60/837,493, filed Aug. 14, 2006.

BACKGROUND OF THE INVENTION

The rapid mutability of HIV-1 has thwarted attempts to create a universal HIV-1 therapeutic immunogenic composition and prophylactic immunogenic composition. However, a transactivating protein termed Tat, which is encoded by HIV-1, secreted by HIV-1 infected cells, and taken up by uninfected CD4+ T cells, is a necessary prerequisite for large scale HIV-1 replication. Resting CD4+ T cells, the main body "tissue" sustaining HIV-1 replication, do not permit HIV-1 replication and Tat activation renders them permissive. Thus, circulating Tat protein presents a promising target for immunological interdiction of an obligatory pathway needed for maintenance of HIV-1 viremia.

The tat gene and its protein have been sequenced and examined for involvement in proposed treatments of HIV (see, e.g., the documents cited in U.S. Pat. No. 6,525,179). Uptake of Tat by cells is very strong, and has been reported as mediated by a short basic sequence of the protein (S. Fawell et al., 1994 Proc. Natl. Acad. Sci., USA, 91:664-668). Prior scientific publications and patent publications by the present inventor established that, although the amino acid sequence of Tat is highly variable, Epitope 1, the immunodominant B cell epitope of Tat, spanning amino acids 4-16, is largely conserved, showing fourfold variation at position 7 (Arg, Lys, Asn or Ser), twofold variation at position 9 (Glu or Asp) and twofold variation at position 12 (Lys or Asn). See, e.g., G. Goldstein, 1996 Nature Med., 2:960; G. Goldstein, 2000 Vaccine, 18:2789; International Patent Publication No. WO 95/31999, published Nov. 30, 1995; International Patent Publication No. WO 99/02185, published Jan. 21, 1999; International Patent Publication No. WO 01/82944, published Nov. 8, 2001; U.S. Pat. Nos. 5,891,994; 6,193,981; 6,399,067; 6,524,582; and 6,525,179; US Published Patent Application Nos. US 2003/0,166,832 and US 2003/0,180,326). Other investigators have subsequently noted some of these variabilities in Tat sequences. See, e.g., Tikhonov et al, 2003 J. Virol., 77(5):3157-3166; Ruckwardt et al, 2004 J. Virol., 78(23):13190-13196; and related International Publications WO2005/062871 and WO2004/056316, among others.

Both monoclonal and polyclonal antibodies to Tat protein have been produced in animals and shown to block uptake of Tat protein in vitro and such monoclonal or polyclonal antibodies to Tat protein added to tissue culture medium have attenuated HIV-1 infection in vitro (see, e.g., documents cited in U.S. Pat. No. 6,524,582). Compositions formed of combinations of these antibodies, particularly combinations of an antibody to one Epitope 1 variant with one or more antibodies that each binds a different Epitope 1 variant, are able to bind a large number of Tat variant sequences characteristic of the multiple strains and subtypes of HIV-1, both B and non-B clades. These antibody compositions are designed to passively immunize a subject, i.e., to inhibit HIV-1 infectivity during initial infection and/or lower viral load post seroconversion, thus delaying progression to AIDS. Further, these resulting compositions or mixtures of such anti-Tat antibodies are treatments for many strains and subtypes of the virus, thus obviating the need for different, and strain-specific, therapeutic agents. Much work is ongoing in the development of a variety of passive immunization compositions for the treatment of HIV-1 infection.

Active immunization, in which a composition induces anti-Tat antibodies in the host, offers an alternative approach, both for therapy and for prophylaxis. Such immunization has been proposed by the inventor's own publications, as well as by others. However, to date, there remains a need in the art for new and useful compositions and methods for generating and using "universal" HIV-1 therapeutic immunogenic compositions and prophylactic immunogenic compositions that are capable of inducing an immune response that is sufficient to effectively treat or prevent AIDS. Such a composition would be useful for immunizing subjects chronically infected with human immunodeficiency virus-1 (HIV-1), symptomatic or asymptomatic, to minimize progression to AIDS (therapeutic composition), and also for immunizing non-infected subjects to prevent the establishment of chronic viremia and AIDS following subsequent HIV-1 infection (prophylactic immunization). The unmet need in this art is to provide a therapeutic or prophylactic composition that presents variants of Tat Epitope 1 in a manner sufficient to obtain an induced antibody titer against multiple Tat Epitope 1 variants (and thus multiple HIV-1 strains and subtypes) and which titer is sufficiently high to avoid the need for frequent, repeated re-administrations of the composition.

BRIEF DESCRIPTION OF THE DRAWINGS

FIG. 1 is a graph showing the anti-Tat antibodies with geometric mean titers (GMT) induced by the immunodominant Tat B cell epitope (i.e., Tat Epitope 1; TEP 1) immunogens with no added adjuvant. These results were plotted from immune serums from immunized mice on two rTats containing the two common immunodominant Tat epitope variants, V-D-P-R-L-E-P-W-K (also referred to as REK in acknowledgement of the amino acid residues present in immunodominant Tat epitope positions 7, 9 and 12) SEQ ID NO: 7 and V-D-P-N-L-E-P-W-N (also referred to herein as NEN for the same reasons as above) SEQ ID NO: 11. The immunogens identified under the X axis of FIG. 1 included experimental immunogens (Pam2-QYIK-TEP1 and Pam3-QYIK-TEP1) and less effective immunogens (QYIK-TEP1 and PAM2K-QYIK-TEP1) synthesized as described in Example 1 and identified in that example. The serum of mice immunized with the experimental immunogens showed anti-Tat antibodies with GMTs>50,000, which were dramatically higher than the GMTs of the antibodies induced by the control immunogens. These results demonstrate the need for a lipopeptide cap in the experimental immunogens to obtain humoral enhancement of the immune response, as well as the need for a structurally specific lipopeptide cap, i.e., the use of Pam2K as the lipopeptide was not sufficient to obtain antibodies with the high GMT which were induced by the experimental immunogens.

FIG. 2 is a graph showing the titers of antibodies in the serum of a single mouse immunized with a mixture of all of the experimental immunogens encompassed by the formula (the Tat 1 immunodominant epitope in bold print with single letter amino acid abbreviations with the wobbles in parentheses): Pam3C-S-S-Q-Y-I-K-A-N-S-K-F-I-G-I-T-E-L-S-V-D-P-(R/K/N/S)-L-(E/D)-P-W-(K/N)-H-P-G-S-amide (SEQ ID NO: 50; Tat amino acid residue 7, 9, and 12 "wobbles") vs. all variant recombinant full length Tat (amino acids 1-72) with the variants displayed in order of incidence, from left to right, along the X axis. The predominant rTat variants at amino acids R7, E9 and K12 or N7, E9 and N 12, e.g., REK (B clade) and NEN (non-B-clades) are shaded. The variants are identified in Table 1 and in Example 2. The serum showed geometric mean antibody titers>100,000 on all eight Tat immunodominant epitope variants.

SUMMARY OF THE INVENTION

The compositions and methods described herein are useful as prophylactic and/or therapeutic agents to address this need in the art.

In one aspect, a self-adjuvanting immunogenic composition useful in the prophylaxis of infection by HIV-1 of multiple strains and subtypes is described. This composition includes multiple immunogens, with each immunogen composed of a lipopeptide cap (R2), a universal T helper sequence (R1), and an immunodominant HIV-1 Tat B cell epitope. In one embodiment, each immunogen has the formula: R2-(R1-HIV-1 Tat B cell epitope) (Formula I). According to this formula, R2 has three positional locations in the immunogen. In one embodiment, the R2 lipopeptide cap (See FIGS. 8A-8C) is linked, via its Cys or via an optional linker sequence of up to 10 amino acids, to the a amino group of the amino-terminal amino acid of the T helper sequence R1, which is linked to the amino terminus of the B cell epitope. In another embodiment, the R2 lipopeptide cap is linked via its Cys or its optional linker amino acid(s) to the E-amino group of a lysine residue inserted between R1 T helper sequence and the B cell epitope. In still another embodiment, the R2 lipopeptide is linked via its Cys or its optional linker amino acid(s) to the ε-amino group of a lysine residue inserted at the C terminus of B cell epitope of the immunogen.

In yet other embodiments, the R1 helper sequence and B cell epitope may be in reverse order, with the R2 lipopeptide cap linked via its linker amino acid(s) in any one of three above-noted positions. Still other orders of arrangement of the immunogen components are contemplated, such as by the alternative formulae disclosed herein.

In some embodiments, the R2 lipopeptide cap comprises a linker of one to ten neutral amino acids to link to the other components of the immunogen. In other embodiments a similar linker is employed to link other components of the immunogen together.

In further embodiments, a sequence of charged, polar amino acids provided with or without the linker sequence is present in various positions in the immunogen. In one embodiment, charged polar sequence is inserted after the R2 cap's Cys, or between the R2 lipopeptide cap's optional linker neutral amino acids and the R1 helper sequence. In other embodiments a linker alone or with such a polar sequence is inserted between R1 helper sequence and the HIV-1 Tat B cell epitope, in either order. In still further embodiments, a linker alone or with such a polar sequence is inserted at the carboxy terminus of R1 or the HIV-1 Tat B cell epitope, whichever is located at the C terminus of the immunogen. In additional embodiments, a linker alone or with such a polar sequence is inserted at the amino terminus of R1 or the HIV-1 Tat B cell epitope, if either is located at the amino terminus of the immunogen.

Figure 8A:
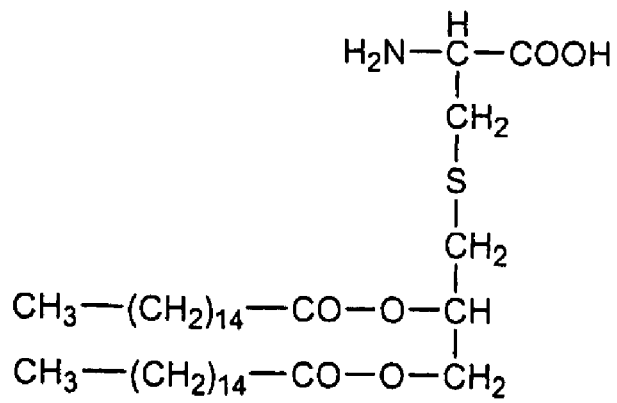
FIG. 8A is a chemical structure of the lipopeptide cap, dipalmitoyl-S-glyceryl cysteine (Pam2C or Pam2Cys).
Figure 8B:
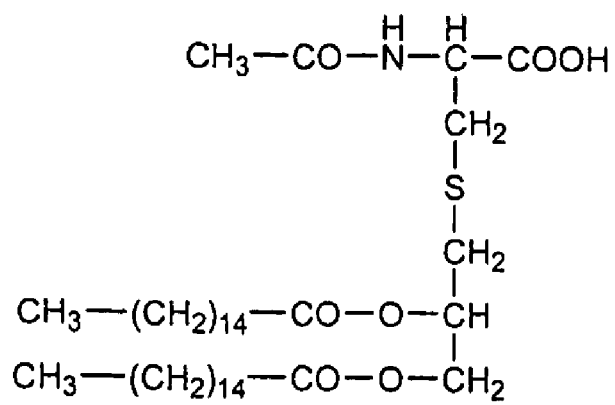
FIG. 8B is a chemical structure of the lipopeptide cap, N-acetyl (dipalmitoyl-S-glyceryl cysteine) (NAc(Pam2Cys) or NAc(Pam2C)).
Figure 8C:
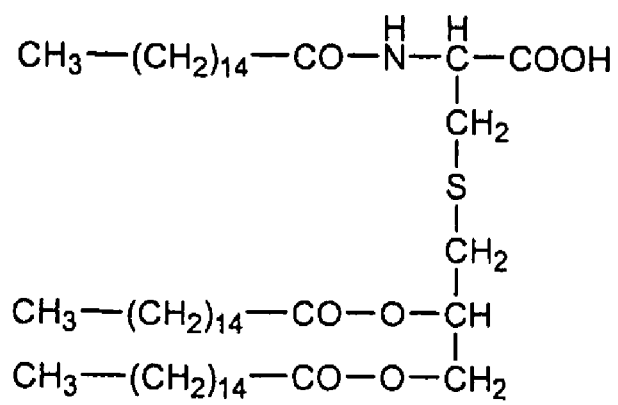
FIG. 8C is a chemical structure of the lipopeptide cap, tripalmitoyl-S-glyceryl cysteine (Pam3C or Pam3Cys).

In certain embodiments, for each immunogen, R2 is dipalmitoyl-S-glyceryl cysteine (Pam2Cys) of FIG. 8A comprising optionally one or up to ten neutral linker amino acids, as described below. In certain embodiments for each immunogen, R2 is N-acetyl (dipalmitoyl-S-glyceryl cysteine) (NAc-(Pam2C) of FIG. 8B, which also can comprise an optional linker amino acid linker. In certain embodiments for each immunogen, R2 is a lipopeptide tripalmitoyl-S-glyceryl cysteine (Pam3Cys) of FIG. 8C, which can optionally comprise a linker sequence.

In an embodiment of these immunogenic compositions, each immunogen of the broad formula above differs from another immunogen of the same formula in said composition by an amino acid variation at amino acid position Xaa7, Xaa9 or Xaa12 of the immunodominant HIV-1 Tat epitope (i.e., Epitope 1). In an embodiment of these immunogenic compositions, multiple immunogens of the broad formulae herein which differ in the arrangement of the R1, R2 and HIV-1 Tat B cell epitope components or which differ in the identity of the R1 and/or R2 (Pam2Cys or NAc(Pam2)C or Pam3Cys) components can be combined in admixture. Such compositions induce anti-HIV-1 Tat antibodies reactive with multiple variants of the HIV-1 Tat protein (both B and non-B clades) with geometric mean titers (GMT) of at least 50,000, at least 300,000 or greater than 1 million, when employed to immunize a subject.

In another aspect, a pharmaceutical composition comprises the self-adjuvanting immunogenic compositions defined herein, and a suitable pharmaceutical carrier or excipient. This composition also demonstrates induction of anti-HIV-1 Tat antibodies with GMT greater than 50,000, or greater than 300,000 or greater than 1 million, on multiple immunodominant Tat epitope (i.e., Epitope 1) variants when a mammalian subject is immunized therewith. In other embodiments, this composition also demonstrates induction of anti-HIV-1 Tat antibodies with GMT greater than 1,000,000 and up to 3,000,000 on multiple Tat Epitope 1 variants when a mammalian subject is immunized therewith.

In yet another aspect, a method of inducing in vivo the production of anti-HIV-1 Tat antibodies against multiple HIV-1 strains and subtypes with high GMT by immunizing a subject with an effective antibody-inducing amount of the immunogenic or pharmaceutical compositions described herein. In certain embodiments, the GMT is greater than 50,000 on multiple immunodominant Tat B cell epitope variants. In other embodiments, particularly where the method employs a prime dose and one or more booster dose(s) of the composition, the GMT is considerably higher, e.g., on the order of greater than 100,000, greater than 300,000 or greater than 1,000,000 on multiple immunodominant Tat epitope variants.

In another aspect, use of the immunogens described above in the manufacture of a medicament for the treatment and/or prophylaxsis of HIV-1 infection is provided. The medicament induces in vivo the production of anti-HIV-1 Tat antibodies against multiple HIV-1 strains and subtypes with high GMT In yet another aspect, a method of making the compositions described herein involves introducing equimolar amounts of the variant amino acids designated by Xaa7, Xaa9 and Xaa12 in the above formula in a single synthesis mixture.

In yet another aspect, introduction of charged polar residues in at least one position within the immunogen confers aqueous solubility and facilitates an aqueous and/or lyophilized formulation.

Other aspects and advantages of these methods and compositions are described further in the following detailed description.

DETAILED DESCRIPTION OF THE INVENTION

The compositions and methods described herein address the need in the art for therapeutic and prophylactic immunogenic compositions for use in treating, retarding progression of, and preventing, HIV-1 infection of multiple strains and subtypes in human subjects. In one embodiment these compositions involve the formulation and application of therapeutic and prophylactic therapies that are efficacious against a full range of HIV-1 strains and subtypes. To create a "universal" HIV-1 prophylactic and therapeutic immunogenic composition, i.e., a composition that is effective in interdicting the Tat protein of multiple HIV-1 strains and subtypes and particularly those strains and subtypes that most frequently occur, the inventor overcame multiple challenges. The compositions described herein (1) incorporate the variability within the peptide sequences of the immunogenic epitope(s) to create a universal composition; (2) create a powerful immunogenic moiety acceptable for use in humans; and (3) create an immunogen soluble in aqueous solvents, that can be presented as a lyophilized product easily reconstituted with water for injection. In a single immunogen, selected sequences that simultaneously enhance a helper T cell response with a B cell response directed to multiple HIV-1 Tat subtypes and strains are combined with a particularly desirable self-adjuvanting lipoprotein, and the resulting sequences modified to enhance aqueous solubility. This combination results in a composition that elicits extraordinarily high, persistent levels of anti-HIV-1 Tat antibody titers in vivo.

I. Compositions

In one embodiment, the self-adjuvanting immunogenic composition comprising a mixture of different specifically designed immunogens employing HIV-1 Tat peptides, which enable the compositions to induce anti-HIV-1 Tat antibodies with geometric mean titers of greater than 50,000, greater than 300,000, and greater than 1 million against the Tat proteins of multiple strains of HIV-1. Each "immunogen" as used herein is a composition that does not occur in nature, but can be produced by synthetic technologies, e.g., chemical synthetic techniques for nucleic or amino acids. This chemical synthesis is completely scalable, allowing for a relatively inexpensive process for producing large quantities of immunogen. It is also possible that recombinant DNA preparation and expression may also be employed to construct some portions of the immunogen, at the selection of the person of skill in the art.

In one embodiment, an immunogenic composition comprises one or more immunogens, each immunogen including a lipoprotein cap (R2), a universal T helper sequence (R1) and an immunodominant HIV-1 Tat protein B-cell epitope. These immunogen components are described in detail below. In a further embodiment, an immunogenic composition comprises one or more immunogens of

| | |
|---|---|
| R2-(R1-HIV-1 Tat B cell epitope), or alternatively | Formula I |
| R2-(HIV-1 Tat B cell epitope-R1), or alternatively | Formula II |
| R2-K(HIV-1 Tat B cell epitope)-R1, or alternatively | Formula IIIa |
| R2-K(R1)-HIV-1 Tat B cell epitope. | Formula IIIb |

In each Formula I and II, the R2 lipopeptide cap may take one of three positions, as described herein. In one embodiment, the R2 cap is linked to the α-amino of an N-terminal amino acid of either R1 (Formula I) or the B cell epitope (Formula II) via the R2Cys or its optional linker amino acid(s). In other embodiments of the above formulae, an optional lysine residue (K) is inserted between the R1 T helper sequence and the B cell peptide (Formula I), the B cell peptide and R1 (Formula II), at the C-terminal end of R1 (Formula II) or at the C-terminal end of the HIV-1 Tat B cell epitope (Formula I). The R2 is linked to the ε-amino group of the inserted K via the R2Cys or its optional linker amino acid(s) in these latter embodiments.

In Formulae IIIa, the K is an inserted lysine residue. The B cell epitope within the parentheses is attached at its carboxy terminus to the ε-amino group of the K. The amino terminus of the R1 is attached directly to the carboxy terminus of the K residue. Similarly, in Formulae IIIb, the K is an inserted lysine residue. The R1 within the parentheses is attached at its carboxy terminus to the ε-amino group of the K. The amino terminus of the B cell epitope is directly attached to the carboxy terminus of the K residue.

In certain embodiments, R2 includes a neutral amino acid sequence or linker sequence of from 0 to 10 amino acids in length, which links the lipopeptide of R2 to the other components forming the immunogen. In other embodiments, an optional linker occurs at the amino or carboxy terminus of the R1 or at the amino or carboxy terminus of the B cell epitope, depending upon the formula selected. In other embodiments, a charged polar amino acid sequence is inserted into the immunogen formula with or without flanking linker amino acids, between the components of the formula or at the carboxy terminus of the immunogen to enhance solubility. The linker and polar charged sequences are described in detail below.

The immunogens described herein can form a variety of structures, based upon the selection of the formula above. In one embodiment of an immunogen of Formula I, the R2 lipopeptide cap, which contains a Cys and optionally one or more neutral linker amino acids, is linked to an α-amino group at the amino terminus of the R1 T helper sequence, which is linked to the B cell epitope, thus forming a linear construct. An optional polar charged sequence is located after the R2Cys, or between the R2 linker amino acids, thus linking to R1, but may also be located at additional positions at the amino or carboxy terminal ends of R1 and the B cell epitope of the immunogen to enhance solubility. Immunogens of this formula are described in the examples below. In another embodiment of an immunogen of Formula I, R2 is linked via its Cys or its optional linker amino acids only and/or via a charged, polar sequence optionally flanked by neutral linker amino acids, to an ε-amino group of a K residue located between R1 and the first N-terminal amino acid residue of the B cell epitope. In still another embodiment of an immunogen as defined by Formula I, R2 is linked via its Cys, its optional linker amino acid(s) and/or polar charged sequence to an ε-amino group of a K residue located at the C terminus of the B cell epitope.

Still other embodiments of immunogens as described herein can take form of Formula II. In most embodiments, the amino terminal end of the R2 lipopeptide cap is free, i.e., not bound between R1 helper sequence and the HIV-1 Tat B cell epitope. In one embodiment of an immunogen of Formula II, the R2 lipopeptide cap with its optional linker amino acid(s) and/or polar charged amino acid sequence, is linked to an α-amino group at the amino terminus of the HIV-1 Tat B cell epitope, which is linked to the R1 helper sequence. In another immunogen of Formula II, the R2 lipopeptide cap is linked via its Cys, its optional linker amino acid(s) and/or its polar charged sequence, or a combination of same, to an ε-amino group of a K residue located between the HIV-1 Tat B cell epitope and the first N-terminal amino acid residue of R1. In another embodiment, the R2 lipopeptide cap is linked as described above to an ε-amino group of a K residue located at the C terminus of the R1 in Formula II. Optional linker and/or polar charged sequences may be located between one or more of these immunogen components. Other alternative immunogens may be designed employing these components and formulae by one of skill in the art given the teachings of this specification.

In one embodiment, an immunogenic composition contains a single immunogen or multiple identical immunogens defined by one of the above-identified formulae. In another embodiment, two or more different immunogens are present in the compositions. In a further embodiment, the two or more immunogens are each of a different formula. In an embodiment containing two or more different immunogens, either of the same or different formula (e), each immunogen in the composition differs from another immunogen in the composition by an amino acid variation at amino acid position Xaa7, Xaa9 or Xaa12 of the immunodominant HIV-1 Tat B cell epitope. Thus, one embodiment of an immunogenic composition contains two such immunogens of the above Formula I or II. In another embodiment an immunogenic composition contains three or more such immunogens. In further embodiments, the immunogens have HIV-1 Tat epitopes which differ from other of the HIV-1 Tat epitopes in other immunogens of Formula I or II in the composition by an amino acid variation at one or more of the variable amino acid positions at positions 7, 9 or 12 in the Tat epitope discussed below. In other embodiments, immunogenic compositions contain at least 2, 3, 4, 6, 8, 12, or at least 16 different immunogens which differ by an amino acid variation at one or more of these amino acid positions of the immunodominant HIV-1 Tat epitope in the formulae. In certain embodiments, the immunogenic compositions contain at least 3, 4, 5, 6, 7 or 8 immunogens with differing immunodominant HIV-1 Tat epitope peptides at those variable residues.

In other embodiments, compositions have two or more immunogens that differ in the identity of R1, the T cell helper sequence. In still other embodiments, different immunogens in a composition may each bear the same or a different R1. In another embodiment, each immunogen in the composition may have a different formula, e.g., one of Formula I, II, IIIa and/or IIIb.

A. The HIV-1 Tat Epitope 1 Component

The HIV-1 Tat B cell epitope of the above immunogen is an immunodominant epitope of the Formula IV: V-D-P-Xaa7-L-Xaa9-P-W-Xaa12-Xaa13-Xaa14-Xaa15-Xaa16 (SEQ ID NO: 1). In Formula IV, Xaa7 is one of the amino acids R, K, N or S. Xaa9 is either an E or D amino acid. Xaa12 is either a K or N. The amino acids of Xaa13-Xaa16 represent an optional flanking sequence included in the immunogen. One or more of the amino acids of Xaa13-Xaa16 may be absent. These amino acids enhance immunogenicity, but are not an essential part of the immunodominant epitope. Thus, the HIV-1 Tat epitope of Formula IV may be referred to herein variously either without Xaa13-Xaa16 or with these four residues present. Thus, in some embodiments, Xaa13 is absent or H; Xaa14 is absent or P; Xaa15 is absent or G and Xaa16 is absent or S.

Of the 16 possible variants formed by various selections of amino acids at positions 7, 9 and 12, eight (8) of the variants are known to be immunologically distinct wild-type variants. The remaining eight other variants are known to occur in nature. The eight immunologically distinct variants of the immunodominant peptide are identified using a shorthand reference identifying only the amino acids at 7, 9 and 12 as shown in Table 1. The same epitope peptides listed in Table 1 below, when flanked by the H-P-G-S sequence, are identified as SEQ ID Nos. 15-22, respectively. These shorthand references are used through out this specification:

TABLE 1

| Shorthand Reference | Sequence | SEQ ID NO: |
|---|---|---|
| REK | V-D-P-R-L-E-P-W-K | 7 |
| KEK | V-D-P-K-L-E-P-W-K | 8 |
| SEK | V-D-P-S-L-E-P-W-K | 9 |
| NEK | V-D-P-N-L-E-P-W-K | 10 |
| NEN | V-D-P-N-L-E-P-W-N | 11 |
| NDN | V-D-P-N-L-D-P-W-N | 12 |
| KEN | V-D-P-K-L-E-P-W-N | 13 |
| SEN | V-D-P-S-L-E-P-W-N | 14 |

Thus, in one embodiment, the immunodominant HIV-1 Tat B cell epitope of the immunogens forming the composition is selected from among these eight peptides without optional flanking sequences. In other embodiments, the eight peptides in the immunogens include the residues H-P-G-S (SEQ ID NO: 4) at the C termini of each peptide to enhance immunogenicity. In still other embodiments, one or more of the peptides contains only one, two, or three of the flanking amino acids. In still other embodiments, a mixture of B cell epitope peptides containing none, one, two, three or four of the flanking amino acids are employed in the immunogens.

In one embodiment, in which the composition contains a single immunogen, one of the above immunogens is employed. In additional embodiments of compositions defined herein, at least 2, at least 3, 4, 5, 6, 7 or 8 of the above Tat variant epitopes of Formula IV are contained in individual immunogens forming the various embodiments of the self-adjuvanting compositions.

Depending upon how the compositions are generated, another immunogenic composition may contain more than eight different HIV-1 Tat epitope peptides. Thus, a composition may contain from 8 to 16 possible different immunodominant HIV-1 Tat epitope variant sequences that differ at amino acid positions Xaa7, Xaa9 and Xaa12, thereby adding to the eight peptides above, the following additional peptide components. These additional eight variants, without the flanking amino acids are reported in Table 2 below with the shorthand references used through out this specification.

TABLE 2

| Shorthand Reference | HIV-1 Tat Epitope I Sequences | SEQ ID NO: |
|---|---|---|
| RDK | V-D-P-R-L-D-P-W-K | 24 |
| KDK | V-D-P-K-L-D-P-W-K | 25 |
| NDK | V-D-P-N-L-D-P-W-K | 26 |
| SDK | V-D-P-S-L-D-P-W-K | 27 |
| REN | V-D-P-R-L-E-P-W-N | 28 |
| RDN | V-D-P-R-L-D-P-W-N | 29 |
| KDN | V-D-P-K-L-D-P-W-N | 30 |
| SDN | V-D-P-S-L-D-P-W-N | 31 |

As previously mentioned, in certain embodiments, the HIV-1 Tat epitopes in the immunogens of these compositions also contain the flanking sequence H-P-G-S on the carboxy terminus of each epitope to enhance the immunogenicity of the HIV-1 Tat epitope in the compositions. The same epitopes as listed in Table 2 with the flanking sequences are identified as SEQ ID NOs: 32-39, respectively.

Thus, in one embodiment, the immunogenic composition contains from 1 up to 16 different immunogens for each of Formulae I-II, which differ in the immunodominant HIV-1 Tat B cell epitope of the immunogen. In a further embodiment, additional variability may be introduced by the presence of the flanking amino acids Xaa13-Xaa16 at the terminus of the immunodominant HIV-1 Tat B cell epitope.

The resulting immunogens that may be present in the compositions are defined by Formula I individually (with the R2 in one of the three positions as described above, and including optional linkers and/or polar, charged sequences in one or more positions as described herein) as follows:

R2-(R1-SEQ ID NO: 15),
R2-(R1-SEQ ID NO: 16),
R2-(R1-SEQ ID NO: 17)

R2-(R1-SEQ ID NO: 18)
R2-(R1-SEQ ID NO: 19),
R2-(R1-SEQ ID NO: 20),
R2-(R1-SEQ ID NO: 21),
R2-(R1-SEQ ID NO: 22),
R2-(R1-SEQ ID NO: 32),
R2-(R1-SEQ ID NO: 33),
R2-(R1-SEQ ID NO: 34),
R2-(R1-SEQ ID NO: 35),
R2-(R1-SEQ ID NO: 36,
R2-(R1-SEQ ID NO: 37),
R2-(R1-SEQ ID NO: 38), and
R2-(R1-SEQ ID NO: 39).

The first eight immunogens in this list above having the HIV-1 Tat epitopes of SEQ ID NOs 15-22, respectively, are the most preferred for compositions containing from one to eight different immunogens. In compositions containing nine or more immunogens, the additional immunogens are selected from among the last eight immunogens in the list. However, other combinations of the B cell epitopes from this list are also useful in the immunogens described herein.

Similar resulting immunogens that may be present in the compositions are defined by Formula II individually (with the R2 in one of the three positions as described above, and including optional linkers and/or polar charged sequences in one or more positions as described herein) as follows:
R2-(SEQ ID NO: 15-R1 amide),
R2-(SEQ ID NO: 16-R1 amide),
R2-(SEQ ID NO: 17-R1 amide),
R2-(SEQ ID NO: 18-R1 amide),
R2-(SEQ ID NO: 19-R1 amide),
R2-(SEQ ID NO: 20-R1 amide),
R2-(SEQ ID NO: 21-R1 amide),
R2-(SEQ ID NO: 22-R1 amide),
R2-(SEQ ID NO: 32-R1 amide),
R2-(SEQ ID NO: 33-R1 amide),
R2-(SEQ ID NO: 34-R1 amide),
R2-(SEQ ID NO: 35-R1 amide),
R2-(SEQ ID NO: 36-R1 amide),
R2-(SEQ ID NO: 37-R1 amide),
R2-(SEQ ID NO: 38-R1 amide), and
R2-(SEQ ID NO: 39-R1 amide).

In one embodiment, a composition contains from three up to eight different immunogens selected from immunogens containing the first eight immunodominant HIV-1 Tat epitope sequences from Table 1 in Formula I, II, IIIa or IIIb above, i.e., SEQ ID NOs: 7 to 14 or SEQ ID NOs: 15-22 with flanking amino acids in the same formulae. Still other compositions contain from 9 up to all 16 different immunodominant HIV-1 epitope peptides from each list, or the immunodominant Tat epitope sequences (with or without the C terminal flanking amino acids) of Tables 1 and 2. In still further embodiments, compositions may include any of the above immunogens having only a one, two, or three of the flanking amino acids.

It is also possible to modify the HIV-1 Tat epitopes in the immunogens described above. For example, other HIV-1 Tat epitopes may include homologous or analogous modified immunodominant epitope sequences, wherein the non-variable amino acids in the formula V-D-P-Xaa7-L-Xaa9-P-W-Xaa12 SEQ ID NO: 2 (i.e., those not represented by a single letter and subscript) may be conservatively replaced individually by amino acid residues having similar characteristics. For example, the non-variable amino acid residues of SEQ ID NO: 2 may be replaced by other amino acid residues bearing the same charge and/or similar side chain lengths. As one example, the leucine at amino acid residue 8 of Tat may be replaced with an isoleucine, as occasionally occurs in the Tat sequence in nature. Similarly the non-variable naturally-occurring amino acids in the SEQ ID NO: 2 may be replaced by unnatural amino acid residues, i.e., an amino acid having a modification in the chemical structure, e.g., a D-amino acid; an amino acid bearing a non-naturally occurring side chains an N-methylated amino acid, etc. See, the cited references relating to N-methylated amino acids, among others. See, e.g., L. Aurelio et al, 2002 Organic Letters, 4(21):3767-3769 and references cited therein.

Further, longer peptides incorporating the Tat amino acid residues of 4-12 of the immunodominant epitope formula V-D-P-Xaa7-L-Xaa9-P-W-Xaa12-Xaa13-Xaa14-Xaa15-Xaa16 SEQ ID NO: 1, but containing additional amino acids at the N and/or C termini, may be employed, although such longer sequences are unlikely to provide any functional difference to the immunogens. For example, the HIV-1 Tat epitopes as described above contain 9 HIV-1 Tat amino acid residues in length, without the C terminal flanking amino acids. However, other immunodominant Tat epitope peptides may contain smaller sequences of about 6 of such amino acids (including preferably the variable amino acids 7, 9 and 12), to about 25 amino acid residues in length. Still other immunodominant peptides may contain more of the N-terminal sequence of HIV-1 Tat. Alternatively, the flanking sequence of Xaa13-Xaa16 of H-P-G-S (SEQ ID NO: 4) of the immunodominant HIV-1 Tat epitope may be similarly replaced with another sequence that enhances the immunogenicity of the immunodominant epitope peptide. In still another embodiment, each of the H-P-G-S (SEQ ID NO: 4) amino acids may be independently replaced with modifications as described above for the invariant amino acid residues of immunodominant Tat epitope.

In yet another embodiment, an alternative immunogen may be prepared for use with the immunodominant epitope immunogens described herein. See, for example, the description of alternative immunogens in Example 1 below. The use of such alternative immunogens may enhance the response to HIV-1 Tat induced by the immunogenic compositions containing the immunodominant epitope immunogens described herein.

B. The Universal T Helper Sequence R1

Another component of the immunogens of the immunogenic compositions described herein is a universal T helper epitope used to enhance the immunogenicity of the B cell epitope in the immunogen, i.e., the immunodominant HIV-1 Tat epitope. The term "T helper epitope" is intended to mean a chain of amino acids which, in the context of one or more class II MHC molecules, activates T helper lymphocytes, which enhances the antibody response to the HIV-1 Tat epitope of the immunogen. In certain embodiments, the T helper epitope component of the immunogens is one that is recognized by T helper cells present in the majority of the population. This can be accomplished by selecting peptides that bind to many, most, or all of the HLA class II molecules. These are known as "loosely HLA-restricted" or "promiscuous" T helper sequences. In particular, promiscuous T cell epitopes are used as the R1 moiety in the formulae above. Depending upon the formula of the immunogen selected, the R1 sequence can be linked to the HIV-1 Tat B cell epitope either directly or via an optional linker and/or polar charged sequence either at the amino or carboxy terminus of the Tat epitope.

Also, depending upon the formula of the immunogen selected, the linkage between R1 and R2 is one of the following: R2 via its Cys or its optional linker amino acid(s) and/or polar charged sequence, is linked to the α-amino of the N terminal amino acid of R1. Alternatively R2 is linked via its Cys or its optional linker amino acid(s) and/or polar charged sequence, to the ε-amino group of an additional lysine residue inserted between R1 and the B cell epitope. Still alternatively if R1 is located at the carboxy terminus of the immunogen, R2 may be linked via its Cys or its optional linker amino acid(s) and/or polar charged sequence, to an ε-amino group of a lysine inserted at the carboxy terminus of R1.

Many promiscuous or universal T helper sequences occur naturally in different sources, e.g., microorganisms, or are artificially engineered sequences. Such suitable T cell epitopes are known and may be selected for this use in these immunogens and compositions.

In one embodiment, and as exemplified by the examples below, the R1T helper sequence in an immunogen as described in Formula I or II herein has the sequence, SEQ ID NO: 6: Q-Y-I-K-A-N-S-K-F-I-G-I-T-E-Xaa, wherein said Xaa is absent or L. This sequence is naturally found in the tetanus toxin at amino acids 830-843(844); see, Panina-Bordignon et al. 1989 Eur J Immunol 19:2237. Another such tetanus toxin sequence (aa 947-967 of tetanus toxin) useful as R1 has the sequence SEQ ID NO: 23: F-N-N-F-T-V-S-F-W-L-R-V-P-K-V-S-A-S-H-L-E, or a derivative thereof, such as aa950-969 of Tet toxoid. See, Reece J C et al. 1994 J Immunol Methods 172:241-54. Still other tetanus toxoid T cell helper sequences for use as the R1 of formula I include the sequences SEQ ID NO: 40: I-D-K-I-S-D-V-S-T-I-V-P-Y-I-G-P-A-L-N-I, aa632-651 of Tet toxoid, SEQ ID NO: 41: N-S-V-D-D-A-L-I-N-S-T-K-I-Y-S-Y-F-P-S-V, aa580-599 of Tet toxoid, SEQ ID NO: 42: P-G-1-N-G-K-A-1-H-L-V-N-N-E-S-S-E, aa 916-932 of Tet toxoid, and SEQ ID NO: 43: Z-Y-I-K-A-N-S-K-F-I-G-I-T-E, aa 830-842 of Tet toxoid. For still other universal T cell helper sequences useful as the R1 of the immunogens, see, e.g., Ho et al. 1990 Eur J Immunol 20:477; Valmori et al 1992 J Immunol 149:717-721; Chin et al. 1994 Immunol 81:428, Vitiello et al 1995 J Clin Invest 95:341; Livingston et al. 1997 J Immunol 159:1383; Kaumaya PTP et al. 1993 J Mol Recognition 6:81-94 (1993), and Diethelm-Okita B M et al. 2000 J Inf Dis 175:383-91; all incorporated by reference herein. See also, Raju et al. 1995 Eur J Immunol 25:3207-14 and Diethelm-Okita B M et al. 2000 J Inf Dis 181:1000-9, incorporated by reference herein, which discuss certain diphtheria toxin T cell helper sequences which may be employed as R1 in the immunogens described herein. Still other sequences which may be useful as T helper epitope sequences for R1 of the formulae above are disclosed in Nardin et al. 2001 J Immunol 166:481-9, incorporated by reference herein.

Examples of other T helper sequences that are promiscuous include sequences from antigens such as *Plasmodium falciparum* circumsporozoite (CS) protein at positions 378-398 (D-I-E-K-K-I-A-K-M-E-K-A-S-S-V-F-N-V-V-N-S; SEQ ID NO: 44), and *Streptococcus* 18 kD protein at positions 116 (G-A-V-D-S-I-L-G-G-V-A-T-Y-G-A-A; SEQ ID NO: 45). See, e.g., U.S. Pat. No. 7,026,443, incorporated herein by reference.

The R1 universal T cell helper sequence may also be an artificially engineered sequence, such as the Pan HLA DR-binding (PADRE) molecule (Epimmune, San Diego, Calif.) described, for example, in U.S. Pat. No. 5,736,142 (see, e.g., PCT publication WO 95/07707, incorporated by reference herein). These synthetic compounds are designed to most preferably bind most HLA-DR (human HLA class II) molecules. Other examples include peptides bearing a DR 1-4-7 supermotif, or either of the DR3 motifs. These sequences are recognized by class 2 mixed histocompatibility (MHC) antigens on B cells and macrophages and dendritic cells and enhance B cell production of antigens.

Thus, in one embodiment, the R1T helper sequence is defined by the formula SEQ ID NO: 46: Xaa1-K-Xaa2-V-A-A-W-T-L-K-A-A-Xaa3, wherein Xaa1 and Xaa3 are independently selected from D-Ala or L-Ala, and Xaa2 is L-cyclohexylalanine, Phe or Tyr. These T helper sequences have been found to bind to most HLA-DR alleles, and to stimulate the response of T helper lymphocytes from most individuals, regardless of their HLA type. In one embodiment, R1 has the above formula, in which Xaa1 and Xaa3 are both D-Ala and Xaa2 is cyclohexylalamine. Other PADRE sequences include an alternative of a pan-DR binding epitope that comprises all "L" natural amino acids and can be provided in the form of nucleic acids that encode the epitope. Still other PADRE sequences are disclosed in Vitiello et al. 1995 J Clin Invest 95:341; Alexander J et al. 1994 Immunity 1:751-61; Del Guercio M-F et al. 1997 Vaccine 15:441-8; Alexander J et al. 2000 J Immunol 164:1625-33; Alexander J et al. 2004 Vaccine 22:2362-7; and Agadjanyan M G et al. 2005 J Immunol 174:1580-6, all incorporated by reference herein.

These T helper peptide sequences R1 can also be modified to alter their biological properties. For example, they can be modified to include D-amino acids or other amino acid modifications to increase their resistance to proteases and thus extend their serum half life. Further these promiscuous T cell helper sequences or R1 sequences may further include linker and/or polar charged sequences as discussed below.

One of skill in the art is expected to select from among other known promiscuous T cell helper sequences to design other specific immunogens for immunogenic compositions as described herein. A specific embodiment, described below, illustrates the universal T helper sequence that has been useful within the immunogens at inducing antibodies with high geometric mean titers (GMT) against HIV-1 Tat protein.

C. The Lipopeptide Cap Component R2

Another component of the immunogens described herein is a lipopeptide component, preferably a "lipopeptide cap" (R2), that works, in concert with the other components of the immunogens to induce antibodies with GMT of greater than 50,000, or greater than 300,000 or greater than 1,000,000, needed for the HIV-1 prophylactic and therapeutic immunogenic compositions as described herein. Lipopeptides have been identified as agents capable of priming CTL against viral antigens and also enhancing humoral antibody responses in vivo against certain antigens. Thus, the R2 moiety of the immunogens is selected from among desirable lipopeptide components having attached thereto a Cys and optionally from one up to ten neutral amino acid linker residues and/or optionally a sequence of charged polar amino acids as described below. In one embodiment, the R2 lipopeptide is attached directly or via its optional linker and/or polar charged amino acid(s) to an α-amino group at the amino terminus of the immunogen, i.e., it is attached to the amino terminus of the R1 T cell helper sequence or directly to the HIV-1 Tat epitope, if the R1 is in a different position. In another embodiment of an immunogen, the R2 lipopeptide is attached directly via its Cys or via its optional one up to ten neutral amino acid linker residues and/or optionally a sequence of charged polar amino acids to an ε-amino of a K residue located between R1 and the first N terminal amino acid residue of the HIV-1 Tat epitope. In yet a further embodiment, the immunogen's R2 lipopeptide cap is linked directly via its Cys or via its optional one up to ten neutral amino acid linker residues and/or optionally a sequence of charged polar amino acids to an ε-amino of a K residue located at the C terminus of the immunogen, i.e., the C-terminus of the HIV-1 Tat epitope or R1. In yet a further embodiment, the immunogen's R2 lipopeptide cap is linked directly via its Cys or via its optional one up to ten neutral amino acid linker residues and/or optionally a sequence of charged polar amino acids directly to a K residue, which is linked directly to the N terminus of either the B cell epitope or the R1. In this structure, either the B cell epitope or the R1 may be linked via its carboxy terminus to the ε-amino group of the K residue (see Formulae IIIa or IIIb).

Specific R2 lipopeptides for such use include, e.g., N-terminal sequences of the *E. coli* lipoproteins. In one embodiment, R2 is a lipopeptide which is dipalmitoyl-S-glyceryl cysteine (Pam2Cys) of FIG. 8A with two amino acid linkers and/or a polar charged sequence. In another embodiment, R2 is a lipopeptide which is tripalmitoyl-S-glyceryl cysteine (Pam3Cys) of FIG. 8C with its amino acid linker and/or polar charged sequence.

Other R2 caps include a R-(dipalmitoyl-S-glyceryl) cysteine, wherein the R is a group consisting of a hydrogen, an alkyl, alkenyl or alkynl of 1-6 C atoms. In one embodiment, R2 is a lipopeptide which is N-acetyl (dipalmitoyl-S-glyceryl cysteine) ((NAc(Pam2C)) of FIG. 8B with an optional amino acid linker and/or polar charged sequence (R is N-acetyl). Other potential R2 moieties are hexadecanoic acid, Hda, and macrophage activating peptide, MALP-2.

Such lipopeptide caps may be selected, synthesized and prepared from those described by Deres, et al., 1998 Nature 342:561; Weismuller et al. 1989 Vaccine 7:29; Metzger et al. 1991 Int J Peptide Protein Res 38:545; Martinon et al. 1992 J Immunol 149:3416; Vitiello et al. 1995 J Clin Invest 95:341; Muhlradt et al. 1997 J Exp Med 185:1951; Livingston et al. 1999 J Immunol 162:3088; Zeng et al 2002 J Immunol 169: 4905; Borzutsky et al. 2003 Eur J Immunol 33:1548; Scgjetne et al. 2003 J Immunol 171:32; Jackson et al. 2004 Proc Natl Acad Sci USA 101:15440 Borzutsky et al. 2005 J Immunol 174:6308; Muhlradt P F et al. J Exp Med 11:1951-8 (1997); Obert M et al. Vaccine 16:161-9 (1997); Zeng W et al. Vaccine, 18:1031-9 (2000); Gras-Masse H Mol Immunol 38:423-31 (2001); Zeng W et al J Immunol 169:4905-12 (2002); Schjetne K W et al. J Immunol 171:32-6 (2003); Spohn R et al. Vaccine 22:2494-9 (2004); Jackson D C et al Proc Natl Acad Sci USA 101:15440-5 (2004); Zeng W et al Vaccine, 23:4427-35 (2005); International Patent Application Publication Nos. WO2006/026834, WO2006/040076, WO2004/014956 or WO2004/014957, all above-cited documents incorporated by reference herein.

In one embodiment, a particularly effective immunogenic composition comprises the R2 of Pam2CSS, i.e., the dipalmitic acid moiety dipalmitoyl-S-glyceryl-Cys, which is attached via a linker, e.g., Ser-Ser, and/or a polar charged sequence. A Pam2C with a linker is described in PCT publication WO 2004/014957, incorporated herein by reference. In another embodiment, a particularly effective immunogenic composition comprises the R2 of Pam3Cys-S-S-, i.e., the tripalmitic acid moiety dipalmitoyl-S-glyceryl-Cys, which is attached via a linker, e.g., Ser-Ser.

In another embodiment, the R2 is NAc(Pam2C)-S-S-, i.e., the dipalmitic acid moiety N-acetyl (dipalmitoyl-S-glyceryl cysteine), which is attached via a linker, e.g., Ser-Ser.

As previously described, this R2 lipopeptide is linked directly via its Cys or via its optional one up to ten neutral amino acid linker residues and/or optionally a sequence of charged polar amino acids, to an α-amino group at the amino terminus of the R1 T cell helper sequence, which is in turn linked to the B cell epitope. If the B cell epitope and T helper sequence are reversed, as in Formula II, this R2 lipopeptide is linked, via its Cys, or its optional linker and/or optional polar charged sequence, to an α-amino group at the amino terminus of the B cell epitope, which is in turn linked to the R1.

Alternatively R2 is linked via its Cys, its suitable linker amino acid(s) and/or polar charged amino acid sequence, to an ε-amino of a K residue located between R1 and the first N terminal amino acid residue of the HIV-1 Tat epitope component of the immunogen. This same structure is dupliciated if the R1 and B cell epitope are reversed, as in Formula II. In still another alternative immunogen structure, the R2 is linked via its Cys, its optional linker amino acid(s) and/or polar charged amino acid sequence to an ε-amino of a K residue inserted at the C terminus of the immunogen. For instance, if the R1 is linked to the B cell epitope, a lysine residue may be inserted at the C-terminus of the B cell epitope and R2 linked to the ε-amino group of that lysine via a linker. This structure is similar if the B cell epitope and R1 group are reversed, as in Formula II. Similarly immunogens of the Formulae IIIa and IIIb are as described above using this R2 cap. In all embodiments, the N terminal end of the R2 lipopeptide cap is free and not bound to another component of the immunogen.

The R2 cap enhances the antibody response, and proves highly effective in the immunogens of Formula I, II, IIIa and/or IIIb that form the immunogenic compositions. Still other embodiments of the variety of attachments of the R2 to the R1 and/or HIV-1 Tat B cell epitopes of the immunogens are embodied in the Formulae I and II described above.

D. The Optional Linkers and Polar Sequences

Although the R2 cap can be directly linked through its Cys, and the T cell helper sequences R1 can be directly linked to the HIV-1 Tat B cell epitope component of the immunogen in either order, a linker is desirably optionally incorporated to link the C terminal end of the R2 lipopeptide cap component to any other component in each immunogen. In other embodiments, linker amino acids or sequences are used also between the B-cell epitope and the R1 helper sequence. In another embodiment, an amino acid sequence is used as an optional linker attached to the N- or C-termini of the R1 helper sequence or the B cell peptide to couple one component to another component of the immunogen, or located at the amino or carboxy terminus of the immunogen, depending upon the formula of the immunogen.

The "linker" located within the R2 cap or positioned elsewhere in the immunogen is typically comprised of from one to ten relatively small, neutral molecules, such as amino acids or amino acid mimetics, which are substantially uncharged under physiological conditions. The linkers are typically selected from, e.g., Gly, Ser, Pro, Thr, or other neutral linkers of nonpolar amino acids or neutral polar amino acids. The optional linker need not be comprised of the same residues and thus may be a heterooligomer, e.g., Gly-Ser- or a homooligomer, e.g., Ser-Ser. When present, the linker in one embodiment is at least one amino acid residues, e.g., Ser or Gly. In another embodiment, the linker is at least two amino acid residues, e.g., Ser-Ser or Gly-Ser. In still other embodiments three to six amino acid residues, and up to 10 or more residues are used to form the linker. Thus in certain embodiments, the linker sequence includes at least 1, 2, 3, 4, 5, 6, 7, 8, 9 or 10 amino acids or mimetics.

For example, a linker may be used to couple the lipopeptide cap of R2 to another component of the immunogen. In one embodiment, the linker is the dipeptide Ser-Ser. In another embodiment, the linker is Gly-Gly. In still another embodiment, a heterooligomer, such as Gly-Ser, or Ser-Gly may be used. In another embodiment, a linker such as -Ser-links the T helper sequence R1 to the N-terminal amino acid of the B cell epitope in the immunogen or links the B cell epitope to the N-terminal amino acid of the R1.

In another embodiment of the immunogens, a sequence of charged, polar amino acids is incorporated within, or replaces, the relatively uncharged linker sequences. Introduction of a charged, polar sequence has been found to enhance the aqueous solubility of the composition, as demonstrated by the examples below. For example, these charged polar sequences are employed to enhance the solubility of the immunogens in formulation with water for injection and optionally mannitol for tonicity, without the need for a buffer. These charged polar sequences enable the immunogens to be readily prepared, solubilized and lyophilized. These polar sequences, by enhancing solubility, may also be useful to enhance the immunogenicity of the B cell epitope.

In one embodiment, the polar sequence is composed of 4, 5, 6, 7, or 8 charged polar amino acids. In a further embodiment, the polar sequence is composed of 4 amino acids. In yet another embodiment, the polar sequence is composed of 6 amino acids. In one embodiment, the polar sequence is composed of amino acids selected from lysine, arginine, aspartate, and glutamate. In a further embodiment, the polar sequence is composed of amino acids selected from lysine, arginine, and aspartate. In another embodiment, the amino acids in the polar sequence are identical. In further embodiments, 2, 3, or 4 different amino acids are used in the polar sequence. Thus, in one embodiment, a polar, charged sequence is -Lys-Lys-Lys-Lys-, -Lys-Lys-Lys-Lys-Lys-Lys-, or -Lys-Glu-Lys-Glu- or -Glu-Glu-Glu-Glu-(SEQ ID NOs. 65, 66, 67, and 68, respectively) or any iteration of from 4 to 8 identical or varying polar, charged amino acids.

Optionally, the polar amino acid sequence is flanked on either terminus by an amino acid of the linker to form the sequence -linker amino acid-(polar amino acid)$_n$-linker amino acid-, wherein n is the number of polar amino acids, e.g., from 4 to 8. Alternatively, the polar amino acid sequence may be used without the flanking linker (neutral, uncharged) amino acids. In one embodiment, the linker with a polar amino acid sequence is composed of Ser-Lys-Lys-Lys-Lys-Ser (SEQ ID NO: 64), i.e., a 4 identical amino acid polar sequence within a Ser-Ser linker, or Ser-[Lys]$_4$-Ser (SEQ ID NO: 64). In another embodiment, the amino acid linker containing a polar sequence is Ser-[Lys]$_6$-Ser (SEQ ID NO: 69). In other embodiments, the linker with polar sequence is Gly-[Lys]$_4$-Gly (SEQ ID NO: 70) or Gly-[Lys]$_6$-Gly (SEQ ID NO: 71). In still other embodiments the linker with polar sequence is -Ser-(Lys-Glu-Lys-Glu-)-Ser-(SEQ ID NO: 72). As above, any iteration of this sequence that can be assembled by one of skill in the art given the above definition and the -linker AA-(polar AA)$_n$-linker AA formulae.

In one specific embodiment, therefore, an amino acid linker containing a polar, charged sequence, or the linker alone, or the polar charged sequence alone, is located between the immunogen component R2 and any other component of the immunogen with which it is linked. In another embodiment, the linker and/or polar sequence is located between R1 and any other component of the immunogen. In still another embodiment, the linker and/or polar sequence is located between the B cell epitope and any other component of the immunogen. In another embodiment, a polar sequence may be attached with or without flanking linker amino acids to a free terminus of the B cell epitope or R1, i.e., external to the immunogen, such as to the free N- or C-terminus of a terminal B cell epitope or R1 helper sequence in the immunogen.

In another embodiment, a polar changed sequence with or without flanking linker amino acids is present only once in the immunogen, e.g., attached only to the carboxy-terminal linker -Ser- of the di- or tripalmitic acid moiety of R2, linking R2 to R1 or the B cell epitope or to an inserted lysine in the immunogen. In still another embodiment, linker and/or polar sequences are present in multiple (i.e., 2 or more) positions in the immunogen.

The R1, R2 and B cell epitope components of each immunogen forming the immunogenic composition can also be modified by the addition of linker amino acids and/or polar charged sequences to the termini of each component to provide for coupling to a carrier support or larger peptide, for modifying the physical or chemical properties of the peptide or oligopeptide, or the like.

E. Specific Embodiments

Specific embodiments of immunogens of Formula I, II, IIIa or IIIb are employed in the examples below and also include the following immunogens. In one embodiment, in each immunogen, R2 is formed by two units of the palmitic acid linked via a thiolglyceryl group to a cysteine and an amino acid linker sequence of -S-S- residues, which links the R2 to the first amino acid of the R1T helper sequence. R1 is Q-Y-I-K-A-N-S-K-F-I-G-I-T-E-L (SEQ ID NO: 47) with an amino acid linker of -S-, which links to the N terminal amino acid residue of the immunodominant HIV-1 Tat B cell epitope which contains different amino acid selections at Tat amino acid position 7 (R/K/N/S), amino acid position 9 (E/D), and amino acid position 12 (K/N) as described above. Thus one immunogen of Formula I is defined as follows:

```
SEQ ID NO: 48:
Pam2C-S-S-Q-Y-I-K-A-N-S-K-F-I-G-I-T-E-L-S-V-D-P-(R/K/N/S)-L-(E/D)-P-W-(K/N)-H-P-
G-S-amide.
```

In a further embodiment, a polar sequence of four lysines (underlined) is incorporated in the linker sequence (-S-S-) connecting R2 to R1. This further immunogen of Formula I is defined as follows:

```
SEQ ID NO: 60:
Pam2C-S-K-K-K-K-S-Q-Y-I-K-A-N-S-K-F-I-G-I-T-E-L-S-V-D-P-(R/K/N/S)-L-(E/D)-P-W-
(K/N)-H-P-G-S-amide.
```

In still a further embodiment, a linker containing a polar sequence of four lysines (underlined) is utilized to link R1 helper sequence to the immunodominant HIV-1 Tat epitope component. This further immunogen of Formula I is defined as follows:

SEQ ID NO: 61:
Pam2C-S-S-Q-Y-I-K-A-N-S-K-F-I-G-I-T-E-L-S-<u>K-K-K-K</u>-S-V-D-P-(R/K/N/S)-L-(E/D)-P-

W-(K/N)-H-P-G-S-amide.

In yet a further embodiment, a linker containing a polar sequence of four lysines (underlined) is utilized in two places in the immunogen, i.e., both as part of the R2 linker to link the lipopeptide to the remainder of the sequence and to link R1 to the immunodominant HIV-1 Tat epitope component. This further immunogen of Formula I is defined as follows:-

SEQ ID NO: 62:
Pam2C-S-<u>K-K-K-K</u>-S-Q-Y-I-K-A-N-S-K-F-I-G-I-T-E-L-S-<u>K-K-K-K</u>-S-V-D-P-(R/K/N/S)-L-

(E/D)-P-W-(K/N)-H-P-G-S-amide.

In another embodiment, in each immunogen, R2 is formed by two units of the palmitic acid linked via a glyceryl group to the surfur of an N-acetyl cysteine (see FIG. 8B) and an amino acid linker sequence of -S-S- residues, which links the R2 to the first amino acid of R1. R1 is Q-Y-I-K-A-N-S-K-F-I-G-I-T-E-L (SEQ ID NO: 47) with an amino acid linker of -S-, which links to the N terminal amino acid residue of the HIV-1 Tat epitope which contains different amino acid selections at Tat amino acid position 7 (R/K/N/S), amino acid position 9 (E/D), and amino acid position 12 (K/N) as described above. Thus one immunogen of Formula I is defined as follows:
SEQ ID NO: 49:
NAc(Pam2C-S-S-Q-Y-I-K-A-N-S-K-F-I-G-I-T-E-L-S-V-D-P-(R/K/N/S)-L-(E/D)-P-W-(K/N)-H-P-G-S-amide. In further embodiments, polar sequences are encompassed parallel to the Pam2C containing embodiments reflected above.

In another embodiment, in each immunogen, R2 is formed by two units of palmitic acid linked via a glyceryl group to the sulfur of a palmityl-cysteine and an amino acid linker sequence of -S-S- residues, which links R2 to R1. R1 is Q-Y-I-K-A-N-S-K-F-I-G-I-T-E-L (SEQ ID NO: 47) with an amino acid linker of -S-, which links to the N terminal amino acid residue of the HIV-1 Tat epitope. Thus, another immunogen of Formula I is defined as follows:
SEQ ID NO: 50
Pam3C-S-S-Q-Y-I-K-A-N-S-K-F-I-G-I-T-E-L-S-V-D-P-(R/K/N/S)-L-(E/D)-P-W-(K/N)-H-P-G-S-amide, with the same variable amino acid residues. In further embodiments, polar sequences are encompassed parallel to the Pam2C containing embodiments reflected above.

In an embodiment in which the Pam3CSS- or Pam2CSS- or NAc(Pam2)CSS-containing moiety is coupled to the E-amino of a lysine inserted between the universal T helper sequence and the HIV-1 Tat epitope, an immunogen of Formula I is defined as SEQ ID NO: 51, with the lipopeptide cap attached via the inserted K residue (bolded) as follows:

In further embodiment, the linkers comprising polar sequences as defined above may be inserted in place of the -S- linking the T helper sequence to the immunodominant HIV-1 Tat B cell epitope sequence and/or a polar sequence may be inserted between the Sers (-S-) which connect the Pam2C cap to the F-amino of the lysine inserted between the universal T helper sequence and the HIV-1 Tat epitope. In an embodiment in which the Pam3CSS- or Pam2CSS- or NAc(Pam2)C-S-S-containing moiety is coupled to the ε-amino of a lysine inserted at the carboxy terminus of the immunodominant HIV-1 Tat epitope peptide, an immunogen of Formula I is defined as SEQ ID NO: 52 with the lipopeptide cap attached via a C-terminal inserted K residue (bolded) as follows:

```
Q-Y-I-K-A-N-S-K-F-I-G-I-T-E-L-S-V-D-P-(R/K/N/S)-L-(E/D)
P-W-(K/N)-H-P-G-S-K-amide
                    |
        PaM2C-S-S (or Pam3-C-S-S-or NAc(Pam2)C-S-S).
```

In further embodiment, the linkers comprising polar sequences as defined above may be inserted in place of the -S- linking the T helper sequence to the immunodominant HIV-1 Tat epitope sequence and/or a polar sequence may be inserted between the serines which connect the Pam cap to the ε-amino of the lysine inserted at the carboxy terminus of the HIV-1 Tat Epitope 1 peptide.

In an embodiment in which the Pam3CSS- or Pam2CSS- or NAc(Pam2)C-S-S-containing moiety is coupled to the ε-amino of a lysine inserted between the HIV-1 Tat epitope and the universal T helper sequence, a Formula II immunogen is defined as SEQ ID NO: 53 with the lipopeptide cap attached via an inserted K residue as follows:

```
Q-Y-I-K-A-N-S-K-F-I-G-I-T-E-L-S-K-V-D-P-(R/K/N/S)-L-(E/D)-P-W-(K/N)-H-P-G-S-amide
                              |
              Pam2C-S-S (or Pam3C-S-S or NAc(Pam2)C-S-S).
```

```
V-D-P-(R/K/N/S)-L-(E/D)-P-W-(K/N)-H-P-G-S-K-S-Q-Y-I-K-A-N-S-K-F-I-G-I-T-E-L-
amide                                     |
                              Pam2C-S-S(or Pam3C-S-S or
                                     NAc(Pam2)C-S-S).
```

In further embodiment, the linkers comprising polar sequences as defined above may be inserted in place of the -S- linking the R1T helper sequence to the HIV-1 Tat B cell epitope sequence and/or a polar sequence may be inserted between the -S-S- which connect the Pam cap to the ε-amino of the lysine inserted between the universal T helper sequence and the HIV-1 Tat epitope.

In an embodiment in which the R1 helper sequence is coupled via an inserted K and S to the N terminal amino acid of the HIV-1 Tat immunodominant epitope, and the Pam3CSS- or Pam2CSS- or NAc(Pam2)C-S-S containing moiety is coupled via the ε-amino of the same lysine residue, the immunogen is defined as SEQ ID NO: 54 with the lipopeptide cap attached via an inserted K residue as follows:

```
Q-Y-I-K-A-N-S-K-F-I-G-I-T-E-L-K-S-V-D-P-(R/K/N/S)-L-(E/D)-P-W-(K/N)-H-P-G-S-
amide                          |
                    Pam2C-S-S(or Pam3C-S-S or
                           NAc(Pam2)C-S-S)
```

In further embodiment, linkers comprising polar sequences may be inserted parallel to those described with respect to the Formula I and Formula II embodiments, above.

In another embodiment of Formula III, in which the Pam3CSS- or Pam2CSS- or NAc(Pam2C)-S-S-containing moiety is coupled via an inserted lysine and serine spacer to the N terminal amino acid of the R1 helper sequence, and the HIV-1 Tat B cell epitope is coupled via the ε-amino of the same lysine residue, the immunogen is defined as follows:

```
                 Pam2C-S-S-K-Q-Y-I-K-A-N-S-K-F-I-G-I-T-E-L-amide
                          |
V-D-P-(R/K/N/S)-L-(E/D)-P-W-(K/N)-H-P-G-S.
```

Still other embodiments of the immunogen employ the formula of IIIb. In further embodiments, polar sequences are encompassed parallel to the Pam2C containing embodiments reflected above.

Immunogenic compositions that contain two or more immunogens as above defined, and as illustrated in the examples below, are characterized by the ability to induce in mammalian animals HIV-1 anti-Tat antibodies with a geometric mean titer of greater than 50,000 on multiple HIV-1 Tat variants, as discussed in more detail below. In other embodiments the GMTS are greater than 300,000 or greater than 1,000,000, or greater than 3,000,000, as exemplified in the examples below.

Given the above teachings, one of skill in the art may readily design other immunogens meeting the Formula I, II, IIIa and/or IIIb by selecting from among the components described above.

II. Methods of Making the Immunogens and Immunogenic Compositions

Immunogens may be prepared according to the formula above containing the "wobbles" at the HIV-1 Tat immunodominant epitope amino acid positions 7, 9 and 12 by carrying out a chemical synthesis in solid phase or in solution. Both synthesis techniques are well known to those skilled in the art. For example, such techniques are described in conventional texts such as Atherton and Shepard in "Solid phase peptide synthesis" (IRL press Oxford, 1989), Stewart & Young, SOLID PHASE PEPTIDE SYNTHESIS, 2D. ED., Pierce Chemical Co., 1984) and by Houbenweyl in "Methoden der organischen Chemie" [Methods in Organic Chemistry] published by E. Wunsch Vol. 15-I and II, Stuttgart, 1974, and also in the following articles, which are entirely incorporated herein by way of reference: P E Dawson et al. (Science 1994; 266(5186):776 9); G G Kochendoerfer et al. (1999; 3(6):665 71); et P E Dawson et al., Annu. Rev. Biochem. 2000; 69:923-60. Various automated or computer-programmable synthesizers are commercially available and can be used in accordance with known protocols. Further, individual peptide epitopes can be joined using chemical ligation to produce larger peptides that are still within the bounds of the immunogens of Formula I or II as described herein.

Desirably the synthesis involves building the immunogens in direction from the C terminal towards the N-terminal by first immobilizing the C-terminal-most amino acid residue on a solid support, such as by using Fmoc chemistry using HBTU on RAMAGE resin. During the sequential addition of amino acids, equimolar amounts of the variant amino acids designated by Xaa7, Xaa9 and Xaa12 "wobble" positions are introduced during a single synthesis mixture. The number of "different" HIV-1 Tat immunodominant epitope sequences that are in the resulting immunogenic mixture can be manipulated by controlling the amino acids introduced at these wobble positions. For example, if desired, one may introduce only two residues at position 7, two at position 9 and one at position 12 to obtain a mixture containing only four (2×2×1) different HIV Tat epitope components. In another embodiment, one may introduce three wobbles at position 7, one at position 9 and 2 at position 12 to obtain six (3×2×1) different HIV peptide components. In the same way, the full 16 different Tat sequences may be obtained in a single synthesis mixture by introducing all possible wobble options (4×2×2). Any other variable addition of the wobbles can result in a mixture containing from 1 to 16 different peptide immunogens. The universal T helper sequence is introduced after the HIV-1 Tat epitope is assembled. The synthesis results in a mixture containing from 1 up to 16 different immunogens, differing at the indicated Tat epitope wobble positions.

The lipopeptide cap is then synthesized as a lipoamino acid essentially as described in PCT publication NO. WO2004/014957, incorporated herein by reference. For example, in one embodiment, the Pam2Cys or NAc(Pam2)Cys or Pam3Cys lipopeptide cap is introduced onto the synthetic Tat epitope wobble sequence and T helper sequence by covalently attaching each lipopeptide moiety via the Cys amino acid or via an optional linker and/or polar amino acid sequence of the cap to an alpha-amino group of the N-terminal amino acid of the T helper sequence, or to the epsilon amino group of a lysine introduced between the T helper sequence and the immunodominant Tat B cell epitope wobble peptide or to the epsilon amino group of a lysine introduced at the C terminus of the immunodominant Tat B cell epitope sequence. The resulting immunogen is then cleaved from the resin using standard methods, e.g., trifluoroacetic acid (Reagent K), and optionally converted to a salt, also using conventional methodologies, e.g., a BIO-RAD acetate resin.

The resulting composition contains from one up to 16 different immunogens, each having the lipopeptide cap attached to an α-amino group of the N-terminus of R1 or the B cell epitope, the epsilon amino group of a lysine residue inserted between R1 and the B cell epitope or to a lysine residue inserted at the C-terminus of R1 or to the HIV-1 Tat B cell epitope. In other embodiments, each immunogen can have a different R1 helper. In one embodiment a composition can contain immunogens having the lipopeptide cap at a position different from other immunogens in the composition, such as described in Formula I, II, IIIa or IIIb.

An exemplary synthesis is described in Example 1. By synthesizing the immunogens in this way, one embodiment of the final immunogenic composition contains 16 sequence permutations (4×2×2) which include greater than 95% of the HIV-1 Tat variants that have been reported to date. The immunogenic composition can be minimally purified to remove solvents and reagents. No rigorous purification is likely to be necessary for the compositions to pass safety tests. This synthesized mixture can then be tested in animals, or used in humans, in a partially purified or in unpurified form. However, optional conventional purification schemes may be employed, if necessary.

While the above described synthetic method is desirable for its simplicity, an alternative method of preparing the immunogens involves the use of recombinant DNA technology. As well known in the art, a nucleotide sequence (which encodes the HIV Tat peptides, optional linkers (with or without polar sequences, e.g., for solubility), T cell helper sequences, and linkers for the lipopeptide cap) is inserted into an expression vector, transformed or transfected into an appropriate host cell and cultivated under conditions suitable for expression. These procedures are generally known in the art, as described generally in Sambrook et al., MOLECULAR CLONING, A LABORATORY MANUAL, Cold Spring Harbor Press, Cold Spring Harbor, N.Y. (1989). The attachment of the lipopeptide cap involves synthetic methods as described above.

One of skill in the art may readily generated a variety of immunogenic compositions containing from two to 16 different immunogens containing from one to 16 different HIV Tat epitopes by following these methods. Still other combinations may be obtained if the various components of the immunogen Formula I, II, IIIa or IIIb are modified individually or collectively, as provided above, such as modifications to individual amino acids, uses of optional linker sequences, uses of different T cell helper or lipopeptide caps, uses of larger or smaller Tat peptides, or combinations of different immunogenic compositions made with such modified sequences.

Such immunogenic compositions are able to induce a prophylactic immune response or therapeutic immune response to HIV-1 Tat proteins in vivo by inducing anti-Tat antibodies with geometric mean titers (GMT) sufficient to prevent infection with HIV-1 or at least partially arrest or retard progression of existing disease symptoms. The titer is the reciprocal of the greatest serum dilution that is still detected at a level of mean+8 standard deviations (SDs) of control values. The geometric mean titer (GMT) is determined by converting each titer of two or more sera to $\log_{10}$, and averaging these $\log_{10}$ values. The anti-log of this latter value is the GMT. In most embodiments, the GMT is determined from three or more individual titers. The use of the GMT rather than individual titers minimizes extreme outlying results and thus improves accuracy.

In one embodiment, an immunogenic composition as described above induces anti-HIV-1 Tat antibodies with GMT of greater than 50,000 or greater than 300,000 on multiple Tat immunodominant epitope variants. In certain embodiments immunogenic compositions induce anti-HIV-1 Tat antibodies in vivo with GMT of greater than 100,000 on multiple Tat immunodominant epitope variants. In other embodiments, the antibodies induced have titers that are greater than 500,000 on multiple Tat immunodominant epitope variants. In still other embodiments immunogenic compositions induce anti-HIV-1 Tat antibody with GMT of greater than 1,000,000 on multiple Tat immunodominant epitope variants. Still others induce anti-HIV-1 Tat antibody with GMT of greater than 3,000,000 on multiple Tat immunodominant epitope variants.

The examples below report experiments in laboratory animals that provide evidence of the extraordinary titers induced by immunogenic compositions described herein. Depending upon the selection and composition of other components used in the pharmaceutical compositions and the regimens and routes of administration of these compositions, the induction of such GMT responses is anticipated with compositions other than those specifically exemplified.

III. Pharmaceutical Compositions and Methods of Treatment/Prophylaxis

A pharmaceutical composition containing the above-described immunogens of Formula I, II, IIIa or IIIb is useful for the therapeutic treatment of HIV-1 infection and/or as a prophylactic immunogenic composition. In various embodiments, the pharmaceutical compositions employ a self-adjuvanting immunogenic composition which contains multiple different immunogens of the Formula I, II, IIIa or IIIb above, and a pharmaceutically acceptable carrier. Desirably, the mixture of unpurified immunogenic peptide immunogens prepared as described above are dissolved or suspended in an acceptable carrier, preferably an aqueous carrier.

As defined herein, pharmaceutically acceptable carriers suitable for use in these immunogenic compositions are well known to those of skill in the art. In one embodiment, a preferred pharmaceutical carrier contains water for injection with mannitol added for tonicity at a concentration of about 45 mg/mL. Other possible carriers include, without limitation, and depending upon pH adjustments, buffered water, buffered saline, such as 0.8% saline, phosphate buffer, 0.3% glycine, hyaluronic acid, alcoholic/aqueous solutions, emulsions or suspensions. Other conventionally employed diluents, adjuvants and excipients, may be added in accordance with conventional techniques. Such carriers can include ethanol, polyols, and suitable mixtures thereof, vegetable oils, and injectable organic esters. Buffers and pH adjusting agents may also be employed. Buffers include, without limitation, salts prepared from an organic acid or base. Representative buffers include, without limitation, organic acid salts, such as salts of citric acid, e.g., citrates, ascorbic acid, gluconic acid, carbonic acid, tartaric acid, succinic acid, acetic acid, or phthalic acid, Tris, trimethanmine hydrochloride, or phosphate buffers. Parenteral carriers can include sodium chloride solution, Ringer's dextrose, dextrose and sodium chloride, lactated Ringer's or fixed oils. Intravenous carriers can include fluid and nutrient replenishers, electrolyte replenishers, such as those based on Ringer's dextrose and the like. Preservatives and other additives such as, for example, antimicrobials, antioxidants, chelating agents, inert gases and the like may also be provided in the pharmaceutical carriers. These immunogenic compositions are not limited by the selection of the carrier. The preparation of these pharmaceutically acceptable compositions, from the above-described components, having appropriate pH isotonicity, stability and other conventional characteristics is within the skill of the art. See, e.g., texts such as Remington: The Science and Practice of Pharmacy, 20th ed, Lippincott Williams & Wilkins, publ., 2000; and The Handbook of Pharmaceutical Excipients, $4^{th}$ edit., eds. R. C. Rowe et al, APhA Publications, 2003.

Optionally, the pharmaceutical compositions can also contain a mild adjuvant, such as an aluminum salt, e.g., aluminum hydroxide or aluminum phosphate.

The amounts of immunogens of Formula I, II, IIIa or IIIb in the pharmaceutical formulations can vary widely, i.e., from less than about 0.1 mg/mL, usually at or at least about 2 mg/mL to as much as 20 mg/mL, or alternatively up to 50 mg/mL or more by weight, and will be selected primarily by fluid volumes, viscosities, etc., in accordance with the particular mode of administration selected.

A human unit dose form of the immunogenic composition is typically included in a pharmaceutical composition that comprises a human unit dose of an acceptable carrier, preferably an aqueous carrier, and is administered in a volume of fluid that is known by those of skill in the art to be used for administration of such compositions to humans (see, e.g., Remington's Pharmaceutical Sciences, 17th Edition, A. Gennaro, Editor, Mack Publishing Co., Easton, Pa., 1985).

These compositions may be sterilized by conventional, well known sterilization techniques, such as sterile filtration for biological substances. Resulting aqueous solutions may be packaged for use as is. In certain embodiments in which at least one polar sequence, e.g., -K-K-K-K-(SEQ ID NO: 65), is present in the immunogens of the composition, the aqueous solutions are lyophilized, the lyophilized preparation being combined with a sterile solution prior to administration.

Thus, as yet another aspect is a method of inducing in vivo the production of anti-HIV-1 Tat antibodies against multiple HIV-1 strains and subtypes with GMT of 50,000, of greater the 300,000 or greater than 1,000,000, as provided above. In one embodiment, the pharmaceutical compositions may be therapeutically administered to an HIV-1 infected human for treatment or control of viral infection. Such an infected human may be asymptomatic or symptomatic. The pharmaceutical compositions are useful to reduce chronic viral multiplication in infected subjects and minimize progression to AIDS. Also among such patients are HIV-1 infected pregnant women, neonates of infected mothers, and unimmunized patients with putative exposure (e.g., a human who has been inadvertently "stuck" with a needle used by an HIV-1 infected human). In another embodiment, the pharmaceutical compositions are administered to healthy subjects as a prophylactic immunogenic composition for prevention of HIV-1 infection.

This method involves administering to a subject an effective antibody-inducing amount of the pharmaceutical compositions described herein, so as to induce anti-HIV1 Tat antibody with GMT greater than 50,000, greater than 300,000, greater than 1,000,000 or greater than 3,000,000, against multiple HIV-1 Tat variants. As described above, this method induces antibody with much higher GMT as well. In already infected patients, antibodies block the maintenance of chronic HIV viremia and thus prevent progression to AIDS. The method can involve repeatedly administering the composition but at infrequent intervals, e.g., every 6 months. In healthy patients, the prophylactic immunogenic composition provides the immunized subject with antibodies that block the establishment of a set point of chronic viremia after acute HIV viremia subsides.

In one embodiment of this method, the route of administration of these pharmaceutical compositions is subcutaneous injection. Other suitable routes of administration include, but are not limited to, intramucosal, such as intranasal, oral, vaginal, or rectal, and parenteral, intradermal, transdermal, intramuscular, intraperitoneal, intravenous and intraarterial. The appropriate route is selected depending on a variety of considerations, including the nature of the composition, i.e., as a prophylactic immunogenic composition or as a therapeutic, and an evaluation of the age, weight, sex and general health of the patient and the components present in the immunogenic composition, and similar factors by an attending physician.

Similarly, suitable doses of the self-adjuvanting immunogenic compositions are readily determined by one of skill in the art, whether the patient is already infected and requires therapeutic treatment or prophylactic immunogenic composition treatment, the health, age and weight of the patient. The method and routes of administration and the presence of additional components in the compositions may also affect the dosages and amounts of the compositions. Such selection and upward or downward adjustment of the effective dose is within the skill of the art. The amount of composition required to produce a suitable response in the patient without significant adverse side effects varies depending upon these factors. Suitable doses are readily determined by persons skilled in the art. A suitable dose is formulated in a pharmaceutical composition, as described above (e.g., dissolved in about 0.1 mL to about 2 mL of a physiologically compatible carrier) and delivered by any suitable means. Dosages are typically expressed in a "unit dosage", which is defined as dose per subject, e.g., a unit dosage of 1 mg immunogen. Alternatively dosages can be expressed as amount per body weight of the subject or patient, using the norm for therapeutic conversions as 80 kg body weight. For example, a 1 mg unit dose per subject is equivalent to about 12.5 µg/kg body weight.

In one embodiment, the intended therapeutic or prophylactic effect is conferred by a priming/boosting dosing regimen. For example, the dosage for an initial therapeutic administration or for a first priming therapeutic or prophylactic immunogenic composition administration in one embodiment is a "unit dosage" of less than about 0.01 mg to 100 mg of immunogen. In one embodiment, the unit dosage is 0.01 mg. In another embodiment, the unit dosage is 0.1 mg. In another embodiment, the unit dosage is 1 mg. In still another embodiment, the unit dosage is 10 mg. Thus, the initial priming dosage for a human, in certain embodiments, can range from very low unit dosages of at least about 0.01, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, to higher dosages of at least 1 mg, at least 3 mg, at least 5 mg, at least 7 mg, at least 10 mg, at least 12 mg, at least 15 mg, at least 20 mg. Still other human dosages range from between 21-30 mg, 31-40 mg, 41-50 mg, 51-60 mg, 61-70 mg, 71-80 mg, 81-90 mg and 91-100 mg/70-80 kg subject. Even higher dosages may be contemplated.

In one embodiment, the boosting dosages for either therapeutic prophylactic immunogenic composition or prophylactic immunogenic composition use are the same as the above described priming dosage. The same specific unit dosage or unit dosage ranges as for the priming dosage above may be employed for the boosting dosage. Thus, the boosting dosage for a human, in certain embodiments, can occur in a unit dosage range a "unit dosage" of less than about 0.01 mg to 100 mg of immunogen. In one embodiment, the unit dosage is 0.1 mg. In another embodiment, the unit dosage is 1 mg. In still another embodiment, the unit dosage is 10 mg. Thus, the booster unit dosage for a human, in certain embodiments, can range from very low unit dosages of at least about 0.01, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, to higher dosages of at least 1 mg, at least 3 mg, at least 5 mg, at least 7 mg, at least 10 mg, at least 12 mg, at least 15 mg, at least 20 mg. Still other human dosages range from between 21-30 mg, 31-40 mg, 41-50 mg, 51-60 mg, 61-70 mg, 71-80 mgs, 81-90 mg and 91-100 mg/70-80 kg subject. Even higher dosages may be contemplated.

In alternative embodiments, the boosting dosages are lower than the priming dosage identified above.

In one embodiment, the first "boosting" is administered within weeks of the initial priming dose. In one embodiment, the boosting dose is administered at least 3 weeks after the priming dose, followed by a re-boost administered not earlier than 3 weeks from the preceding boosting dose. In another embodiment, the first boosting dose is administered about 3 to 4 weeks following the priming dose. Additional boosting dosages are administered thereafter at least 3 weeks thereafter, more suitably about 6 months to one or more years, following the first booster dose. In another embodiment of an administration protocol, a priming dosage of a self-adjuvanting immunogenic composition as described herein is administered which is about 10 mg. The subsequent first boosting dosage (e.g., 0.01, 0.1, 1 or 10 mg) is then administered at least three weeks after the priming dosage. Thereafter, additional boosting dosages are administered every 6 months to one year from the preceding boosting dosage.

The timing and dosage of any priming/boosting regimen may be selected by the attending physician depending upon the patient's response and condition as determined by measuring the specific anti-HIV-1 Tat antibody titer obtained from the patient's blood, as well as normal considerations related to the physical condition of the patient, e.g., height, weight, age, general physical health, other medications, etc.

In one embodiment of the prophylactic/therapeutic method involves administering a priming effective amount of the immunogenic composition in a unit dosage of less than or about 10 mg, 1 mg or 0.1 mg, and following up the administration by two boosters administered at weeks 3 and weeks 6 at the same effective unit dosage. This method induces antibodies of a GMT greater than 100,000.

In another embodiment of the prophylactic/therapeutic method involves administering a priming effective amount of the immunogenic composition in a unit dosage of less than or about 10 mg, 1 mg or 0.1 mg and following up the administration by two boosters administered at weeks 3 and weeks 6 at the same effective dosage. This method induces antibodies of a GMT greater than 1,000,000.

Administration desirably continues until at least clinical symptoms or laboratory tests indicate that the viral infection has been eliminated or reduced and for a period thereafter. The dosages, routes of administration, and dose schedules are adjusted in accordance with methodologies known in the art.

For prophylactic immunogenic composition use, the priming and boosting dosages are similar to the boosting dosages of the therapeutic prophylactic immunogenic composition, but are administered at certain defined intervals from about two weeks to six months after the initial administration of prophylactic immunogenic composition. Possibly additional prophylactic immunogenic composition administrations may be desirable thereafter.

As indicated in the examples below, the antibody with high GMT induced by the exemplary pharmaceutical or immunogenic compositions described herein may reduce the need for a high frequency of boosting dosages for either therapeutic or vaccinal use.

In still another embodiment of the methods described herein, the compositions may be used in conjunction with, or sequentially with, other HIV-1 anti-viral therapies or pharmaceutical regimens.

The following examples illustrate certain embodiments of the above-discussed compositions and methods. These examples do not limit the disclosure of the claims and specification.

IV. EXAMPLES

Example 1

Generation of an Immunogenic Composition of the Invention

A. Experimental Immunogens

Various immunogenic compositions as described above were prepared containing multiple different Tat peptide components (bolded), a T cell helper sequence (italicized and bolded), linker amino acids (italicized only) and the Pam2C- or Pam3C- lipoprotein cap according to the formula below (note that the NAc(Pam2)C-S-S capped formula is to be prepared similarly to the Pam2C and Pam3C capped immunogens described by this formula):

SEQ ID NO: 55:

(Pam2C or Pam3C or NAc(Pam2C)-*S-S*-T CELL HELPER-*S*-V-D-P-(R/K/N/S)-L-(E/D)-P-

W-(K/N)-H-P-G-S-amide.

Alternative immunogens are prepared in a similar manner for other similar compositions which are expected to produce similar results. Such similar immunogens include, e.g.,:

SEQ ID NO: 56:

```
T HELPER SEQUENCE-K-V-D-P-(R/K/N/S)-L-(E/D)-P-W-(K/N)-H-P-G-S-amide
                 |
         Pam2C-S-S or Pam3-C-S-S or NAc(Pam2C)-S-S, or
```

SEQ ID NO: 57:

```
                          (or Pam3C-S-S or NAc(Pam2C)-S-S)
                                             Pam2C-S-S
                                                     |
T CELL HELPER-V-D-P-(R/K/N/S)-L-(E/D)-P-W-(K/N)-H-P-G-S-K-amide
```

The Pam2C- and Pam3C immunogens prepared according to the first of the three preceding formulae were synthesized by Bachem Biosciences, Inc. or Mimotopes, Pty. Ltd. using conventional solid phase synthesis techniques and automated synthesizers. Commencing with an amidated C-terminal serine at the C-terminus the cycles of synthesis proceeded towards the N-terminus of the Tat epitope 1, through the linker amino acids, through the helper T cell epitope sequence (which is, e.g., the tetanus toxoid promiscuous T helper sequence Q-Y-I-K-A-N-S-K-F-I-G-I-T-E-L; SEQ ID NO: 47) and through Ser-Ser at the N-terminus. At the positions corresponding to amino acids 7, 9, and 12, the "wobble" positions, equimolar amounts of the 4, 2 and 2 required amino acids, respectively, (in parentheses in the formula above) were added.

Tripalmitoyl-S-glyceryl-cysteine and fmoc protected dipalmitoyl-S-glyceryl-cysteine were synthesized by Bachem and were coupled to the N-terminal serine of the nascent peptide chain as indicated. Trifluoroacetic acid was used to cleave the lipopeptide from the resin and deprotect the peptide. The resulting immunogenic product was dried and then taken into aqueous solution, converted to an acetate salt form and dried.

The final product was checked by amino acid analysis for the appropriate content of amino acids, and by mass spectroscopy, which revealed a complex pattern of peaks. Purity was estimated in general to be around 70%, but the resulting lipopeptide was not purified further. The HIV-1 Tat B cell epitopes used in the immunogens that were synthesized and studied are listed as SEQ ID NOs: 15 through 22 and 32-39 in the two formulae:

```
SEQ ID NO: 48:
Pam2C-S-S-Q-Y-I-K-A-N-S-K-F-I-G-I-T-E-L-S-V-D-P-(R/K/N/S)-L-(E/D)-P-W-(K/N)-H-

P-G-S-amide (identified as Pam2-QYIK-TEP1 in the figures); and

SEQ ID NO: 50
Pam3C-S-S-Q-Y-I-K-A-N-S-K-F-I-G-I-T-E-L-S-V-D-P-(R/K/N/S)-L-(E/D)-P-W-(K/N)-H-

P-G-S-amide (identified as Pam3-QYIK-TEP1 in the figures).
```

B. Control Immunogens

The synthesis procedures described above were also employed to prepare other immunogens for comparison with the immunogens discussed above for use in the following examples. Among such "control" immunogens were an immunogen that contained only the T cell helper sequence fused to the Tat Epitope 1, i.e. a formula of SEQ ID NO: 58: Q-Y-I-K-A-N-S-K-F-I-G-I-T-E-L -S-V-D-P-(R/K/N/S)-L-(E/D)-P-W-(K/N)-H-P-G-S-amide (identified as QYIK-TEP1 in the figures). Similarly, a control immunogen that contained the lipopeptide cap, Pam-2K in place of the Pam-2C of the immunogens described above, i.e., a formula of

SEQ ID NO: 59

Pam2K-S-S- Q-Y-I-K-A-N-S-K-F-I-G-I-T-E-L -S-V-D-P-(R/K/N/S)-L-(E/D)-P-W-(K/N)-H-P-G-S-amide was identified as Pam2K-QYIK-TEP1 in the figures.

Example 2

Immunization Protocol and Tat Reagents

A. Immunizations

Animals were purchased from Harlan Laboratories and acclimated at Molecular Diagnostic Services, Inc. for at least 1 week before immunization. Both BALBc and C57BL61BALBc F1 mice were used. Lewis rats were used as indicated.

Immunogens prepared as described in Example 1 were taken up in buffered saline and injected IP in mice and rats, and SC in rabbits. Unless otherwise stated mice were immunized IP with 1 mg of Immunogen at Day 0 and Week 2 and serums were obtained at Week 4 for titration. Other regimens and species were as noted in the figures.

Table 3 illustrates the immunization protocol and GMT of the animal sera used in the examples below.

TABLE 3

| Animal | Prime Dose | Boosting Dose | GMT |
| --- | --- | --- | --- |
| Mouse | 1 mg | 0.3 mg | 280,000 |
| Rat | 10 mg | 10 mg | 370,000 |
| Rabbit | 10 mg | 10 mg | 61,000 |

Note that the tet toxoid T cell helper sequence used in the immunogens discussed herein was originally discovered as having promiscuous helper activity in human cells and appears to have wide activity in multiple animal species.

B. Recombinant Full-LengthTat rTat-His6 was produced by ATG Laboratories, Inc. The consensus HIV-1 Tat HXBIII sequence was modified by site directed mutagenesis to produce eight full length (AA 1-72) immunodominant Tat variants, which were identified in Table 1 above as REK, KEK, SEK, NEK, NEN, NDN, KEN, NEN and SEN.

Each variant was expressed in *E. coli* and extracted in a non-denatured form and was isolated on a nickel column under non-denaturing conditions. After dialysis to remove imidazole, aliquots were stored frozen at −70° C. These preparations were used for both bioassays and as substrate for antibody titrations of anti-Tat binding as described below.

Example 3

Serum Titrations

Serums were assayed to determine anti-Tat titers by conventional ELISA methods. Briefly, Maxisorp Immuno plates were coated with 2 ng/well rTat and incubated at 22° C. for 1 hour or 4° C. overnight. After thorough washing with 0.1% triton X 100 buffer, blocking with 1% bovine serum albumin (BSA) and rewashing, serum dilutions were applied and incubated at 22° C. for 1 hour. After incubation, the plates were thoroughly washed with triton-X 100 buffer again and 1/10,000 goat anti-mouse IgG-horseradish peroxidase (HRP) conjugate (or the appropriate reagent for rat or rabbit) was applied. The plates were then incubated for 1 hour at 22° C. then washed thoroughly and developed with ABTS for 45 minutes at room temperature on a shaker table. Absorbance was measured at 405 nm. Control wells lacking serum were measured and the titration endpoint was the reciprocal of the lowest dilution with an OD greater than mean+8 SDs.

A. Comparison of Geometric Mean Antibody Titers (GMT) in Animals Immunized with the Experimental Immunogens vs. with Control Immunogens.

Figures 1, 2:
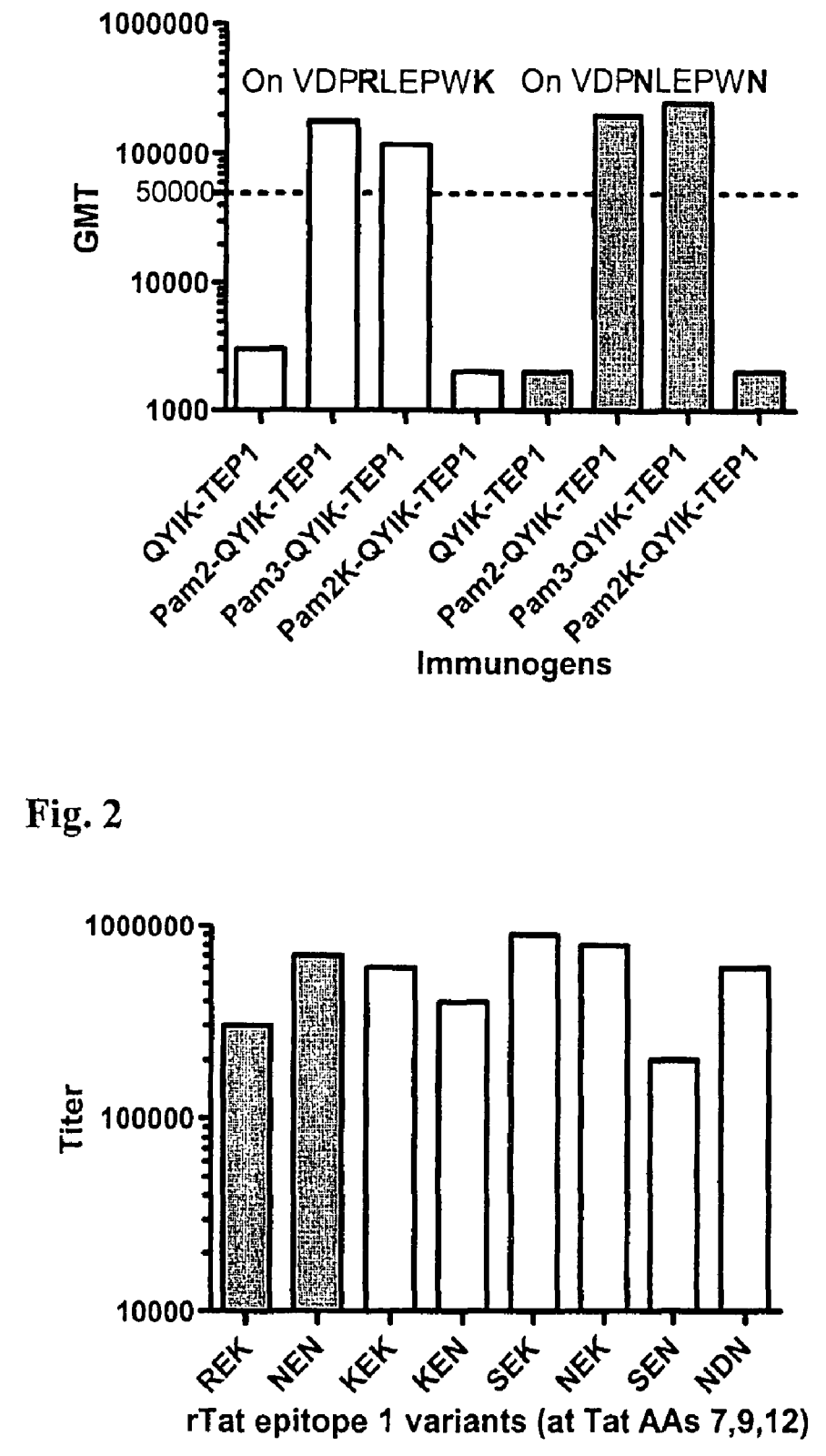

FIG. 1 is a graph showing the geometric mean titers (GMT) of immune serums from immunized mice on two rTats containing the two common Epitope 1 variants, V-D-P-R-L-E-P-W-K (SEQ ID NO: 7) and V-D-P-N-L-E-P-W-N (SEQ ID NO: 11). The immunogens identified under the X axis of FIG. 1 were synthesized as described in Example 1 and are identified in that example. The immunogens used as the T helper sequence either the tetanus toxoid promiscuous T helper sequence described for use in man (Q-Y-I-K-A-N-S-K-F-I-G-I-T-E-L; SEQ ID NO: 47) or the PADRE T helper sequence engineered for promiscuous human DR binding (Xaa1-K-Xaa2-V-A-A-W-T-L-K-A-A-Xaa3; SEQ ID NO:46), wherein Xaa1 and Xaa3 were each D-Alanine, and Xaa2 was L-cyclohexylalanine. The data on the PADRE-containing immunogens is not shown in the figures.

The results of FIG. 1 shows that the immune serums reacted similarly with the two common Tat epitope 1 variants in contrast to the lack of cross reactivity of sera raised to these Tat variants singly. The experimental lipopeptide immunogens induced antibodies that demonstrated GMTs of greater than 50,000. In contrast, immunogens lacking the Pam2CSS- or Pam3CSS- N-terminal cap induced antibodies with maximal GMTs of 2-3,000, including both the immunogens lacking any lipopeptide cap and the immunogen with the Pam2KSS cap.

B. GMT for Animal Immunized with Experimental Immunogen Against rTat Variants

Serum from a single mouse immunized with the experimental immunogens of formula Pam3C-S-S-Q-Y-I-K-A-N-S-K-F-I-G-I-T-E-L -S-V-D-P-(R/K/N/S)-L-(E/D)-P-W-(K/N)-H-P-G-S-amide (SEQ ID NO: 50; Tat amino acid residue 7, 9, and 12 "wobbles") of Example 1 was examined for anti-Tat antibody titer. FIG. 2 is a graph showing the GMT of antibodies in the serum vs. full length variant recombinant Tat proteins displayed along the X axis, i.e., REK, NEN, KEK, KEN, SEK, NEK, SEN and NDN as identified in Table 1 above, i.e., SEQ ID NOs: 15, 19, 16, 21, 17, 18, 22 and 20, respectively.

The Tat variants REK (B clade) and NEN (non-B clades) are the most frequent and are shaded in FIG. 2. The serum showed GMTs>100,000 on all Tat Epitope 1 variants.

C. Effect of Booster Dose of Experimental Immunogen on GMT

Figure 3:
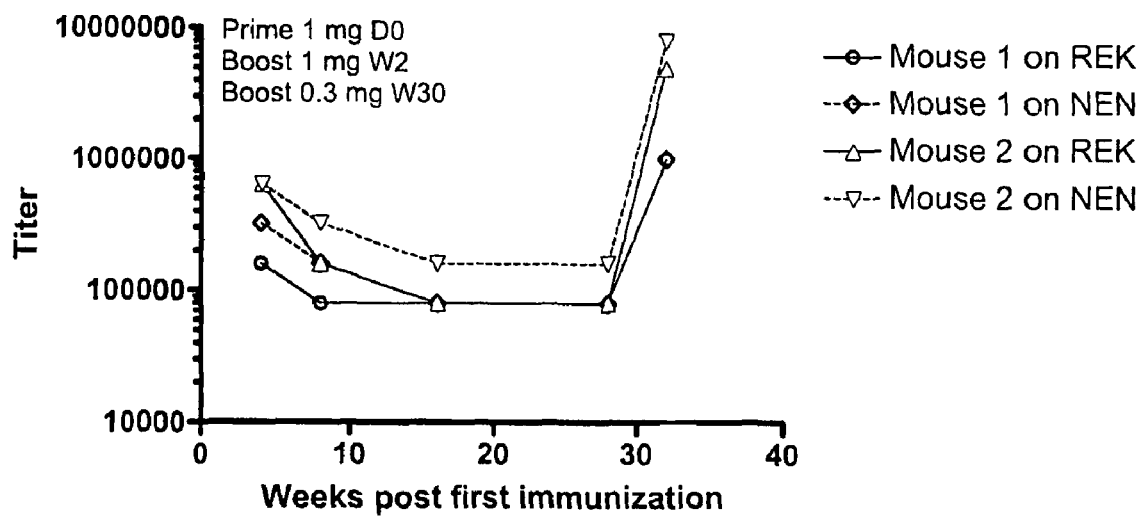
FIG. 3 is a graph showing titers of sequential sera from two mice immunized with experimental immunogen, Pam2C-S-S-mouse T helper sequence-V-D-P-(R/K/N/S)-L-E-P-W-(K/N)-H-P-G-S-amide (SEQ ID NO: 3; Tat amino acid residue 7 and 12 "wobbles") in a protocol of a 1 mg intraperitoneal (IP) priming dose at Day 0, followed by a 1 mg IP booster at Week 2, and a 0.3 mg IP second booster at Week 30. The serums were titered on the immunodominant Tat B cell epitope variants SEQ ID NO: 15: V-D-P-R-L-E-P-W-K-H-P-G-S-(REK) (○, Mouse 1 on REK; and Δ, Mouse 2 on REK) and SEQ ID NO: 19: V-D-P-N-L-E-P-W-N-H-P-G-S-(NEN with the 4 amino acid C terminal flanking sequence-H-P-G-S-) (◇, Mouse 1 on the NEN; and an open inverted triangle for Mouse 2 on NEN). The antibody titers decline somewhat from week 4 to week 16 and remained steady at 80,000 through week 28. The antibody titers show marked elevations 2 weeks after the 30 week 0.3 mg boost. These data demonstrate that the prime-boost regimen can maintain effective levels for at least 4 months, and that an additional late boost will increase titers even further.

Two mice were immunized with experimental immunogen, Pam2C-S-S-mouse T helper sequence-V-D-P-(R/K/N/S)-L-E-P-W-(K/N-H-P-G-S-amide (SEQ ID NO: 3; Tat amino acid residue 7 and 12 "wobbles") in a protocol of a 1 mg intraperitoneal (IP) priming dose at Day 0, followed by a 1 mg IP booster at Week 2, and a 0.3 mg IP second booster at Week 30. The serums were titered on full length Tat variants REK (SEQ ID NO: 15) and NEN (SEQ ID NO: 19). The titers decline somewhat from week 4 to week 16 and remained steady at 80,000 through week 28 then showing a marked elevation 2 weeks after the 30 week 0.3 mg boost. FIG. 3 is a graph showing these results for two mouse sera.

Example 4

Bioassay of Tat Activity and Inhibition by Antibody

A. Bioassay

HIV-1 can enter resting CD4+ T cells but is unable to replicate unless the T cell is activated. Tat activates the CD4+ T cells in human peripheral blood mononuclear cells (PBMC). This Tat-induced activation and permissivity for HIV-1 replication could be inhibited by anti-Tat antibodies, as discussed in Li et al. 1997 Proc Natl Acad Sci USA 94:8116. The bioassay for antibody inhibition of Tat induced permissivity for HIV-1 replication in human PBMC performed as follows is based upon these observations.

PBMC were obtained from Astarte Biologics and comprised 30 frozen PBMC aliquots from the same donor at a given donation. The cells were thawed, diluted appropriately and distributed in 100 µl medium (complete RPMI medium, Gibco) containing 500,000 cells in the flat bottom 96 well tissue culture plate. Appropriate concentrations of rTat or rTat/Ab solutions were added (after pre-incubation for 30 minutes at room temperature). The plates were incubated for 5 days at 37° C. with 5-6% $CO_2$ and 80-90% humidity. At 5 days media was pipetted into the wells to release cells from the plate surface. The cells were transferred to a V-bottom 96 well plate, spun at 400×G (≈1300 rpm) for 10 minutes at RT, then the medium was removed. 100 µl of a 1/10 dilution of stock HIV-1 (HXBIII) (Zeptometrix Corp.) was added and incubated for 4 hours at 37° C. in $CO_2$ incubator. After thorough washing the cells were incubated in medium for an additional 4 days. The cells were then spun, as above, and the medium recovered for ELISA determination of HIV-1 p24 levels (kit from Xeptometrix Corp.) The p24 assay was performed as per the manufacturer's instructions.

Figure 4:
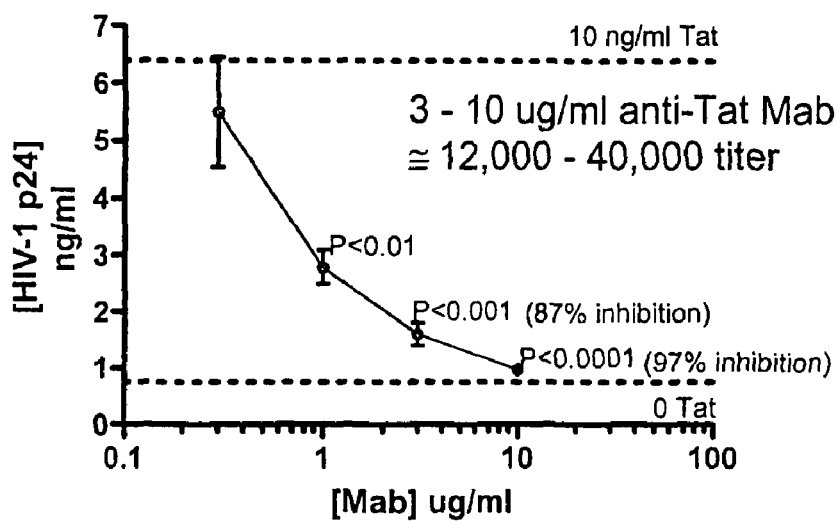
FIG. 4 is a graph of a bioassay for antibody inhibition of Tat induced permissivity for HIV-1 replication in human PBMC as described in Example 4A. The data show anti-Tat MAb inhibition of Tat induced PBMC permissivity for HIV-1 replication. The lower dotted line shows the background HIV-1 p24 level (ng/ml) with no Tat; and the upper line shows the mean HIV-1 p24 level (ng/ml) with 10 ng/ml Tat. A dose-response curve of inhibition is produced, with 3 µg/ml anti-Tat monoclonal antibody (Mab) and 10 µg/ml anti-Tat monoclonal antibody producing 87% and 97% inhibition, respectively, with highly significant statistics (P<0.001 and 0.0001, respectively).

The results of a representative bioassay are shown in FIG. 4. The lower dotted line shows the background HIV-1 p24 level (ng/ml) with no Tat and the upper line shows the mean p24 level (ng/ml) with 10 ng/ml Tat. A dose-response curve of inhibition is produced, with 3 µg/ml anti-Tat monoclonal antibody (Mab) and 10 µg/ml anti-Tat monoclonal antibody producing 87% and 97% inhibition, respectively, with highly significant statistics ($P<0.001$ and $0.0001$, respectively).

Normal mouse serum (NMS) had unpredictable effects in this assay, even in the absence of Tat. Therefore, to generate a titer comparison for the anti-Tat MAb, 10 µg/ml of the MAb was added to NMS. The titer of this "spiked" NMS on Tat was determined as described above in Example 3. 10 µg/ml anti-Tat Mab had a titer of 40,000, which provided an approximation of the serum titers that would be needed in immunized mice to obtain>90% inhibition of Tat-induced HIV-1 replication, i.e., 12,000 to 40,000.

B. Inhibition of Free Tat Concentration by Antibody

Antibody treatment of toxins is predicated on the binding of the toxin by high affinity antibody lowering the concentration of free toxin and thus blocking the toxicities associated with the toxin (Nowalowski et al. 2002 Proc Natl Acad Sci USA 99:11346). This holds true both in vitro and in vivo (ibid). Accordingly, an assay to measure the lowering of free Tat concentrations by anti-Tat MAb and immune anti-Tat serum was performed to verify with independent methodology the above-identified estimates of titers required to control HIV-1 replication in vivo.

The principle of this Tat ELISA assay is to bind the anti-Tat MAb or anti-Tat immune serum, in parallel with normal IgG or NMS controls, with protein A coated beads (Pierce ImmunoPure Protein A plus resin). This was done at the required dilutions and the tubes were incubated on the tube rotator for at least 1 hour at RT. The tubes were then spun at 6,000 rpm in the microfuge for 30 seconds to pellet the resin and remove the serum sample. The resin was then washed thoroughly; the Tat solution (200 ng/ml) was added; and the tubes were incubated on the tube rotator for at least 1 hour at RT. The tubes were then centrifuged at 6,000 rpm for 30 seconds to pellet the resin and the supernatant was removed to a fresh tube for analysis.

The Tat ELISA utilizes a high affinity anti-immunodominant Tat epitope MAb for the plate coating and a polyclonal rabbit anti-Tat Epitope 2 (1/4,000) as the detector antibody. The Epitope 2 sequence is the conserved HIV-1 Tat sequence K-(A/G)-L-G-1-S-Y-G-R-K (SEQ ID NO: 5). rTat (Example 2) is used to generate a standard curve. The unbound Tat concentration in the test and control supernatants are then used to calculate the % inhibition of free Tat concentration in the anti-Tat exposed conditions by comparison with the control concentration.

Figure 5:
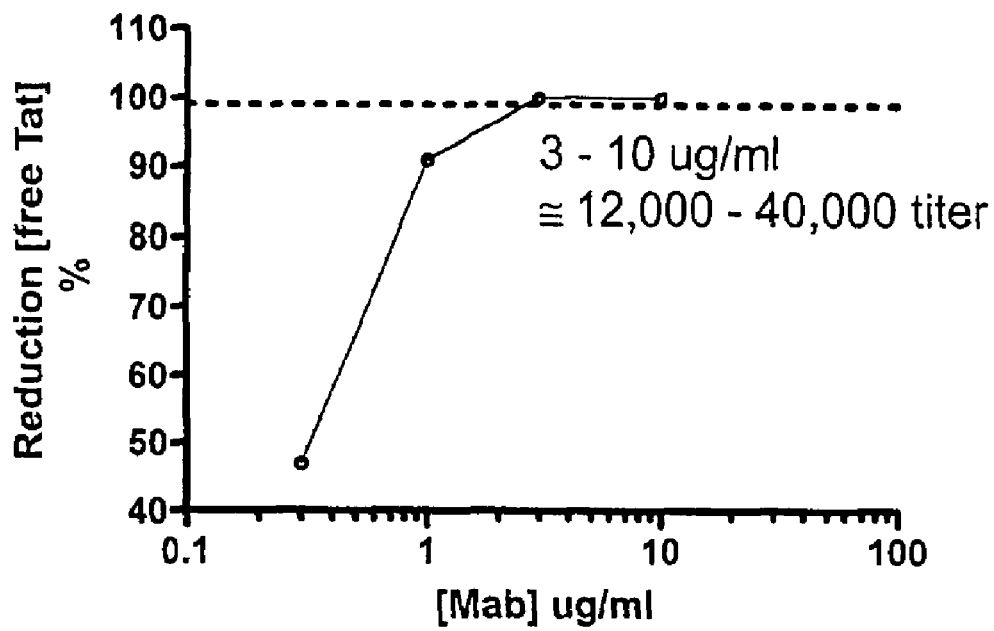
FIG. 5 is a graph showing the % inhibition or reduction of the free Tat concentration by the same anti-Tat MAb used in FIG. 4 in the ELISA of Example 4B. Full inhibition is observed over the 3-10 µg/ml range, corresponding to an antibody titer on Tat of 12,000 to 40,000.
Figure 6:
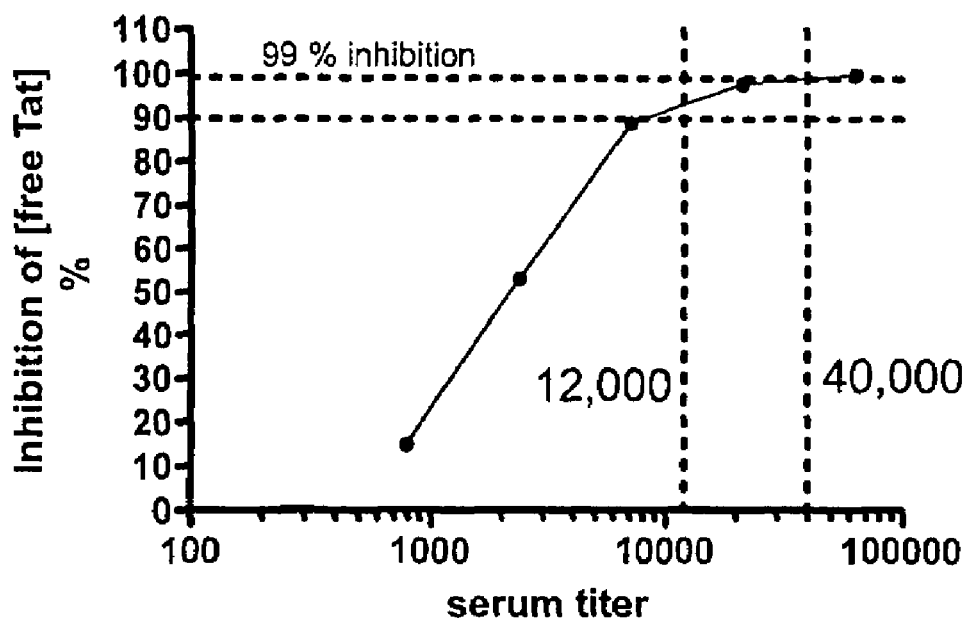
FIG. 6 is a graph showing the % inhibition or reduction of free Tat concentration by dilutions of a high titer mouse anti-Tat serum in the ELISA of Example 4B. Maximal inhibition of free Tat concentration occurs in the 12,000 to 40,000 titer range.

FIGS. 5 and 6 demonstrate the validity of previous estimation of the required titers of 12,000 to 40,000 to control HIV-1 replication in vivo using such assay experiments. FIG. 5 shows the % inhibition of free Tat concentration by the anti-Tat Mab, with full inhibition over the 3-10 µg/ml range, corresponding to a titer on Tat of 12,000 to 40,000 (see above). FIG. 6 shows a similar experiment performed with dilutions of a high titer (640,000) mouse anti-Tat serum. Again maximal inhibition of free Tat concentration occurs in the 12,000 to 40,000 titer range.

A similar second ELISA experiment was carried out in quintuplicate at 10% and 1% dilutions of Tat-immune and normal mouse sera; the Tat antibody titer of the immune serum was 256,000 on each of the two recombinant Tat proteins having either the immunodominant epitope REK (SEQ ID NO: 7) or NEN (SEQ ID NO: 11) sequence, the two most common forms. Reductions of both Tat variants were studied.

Figure 7A:
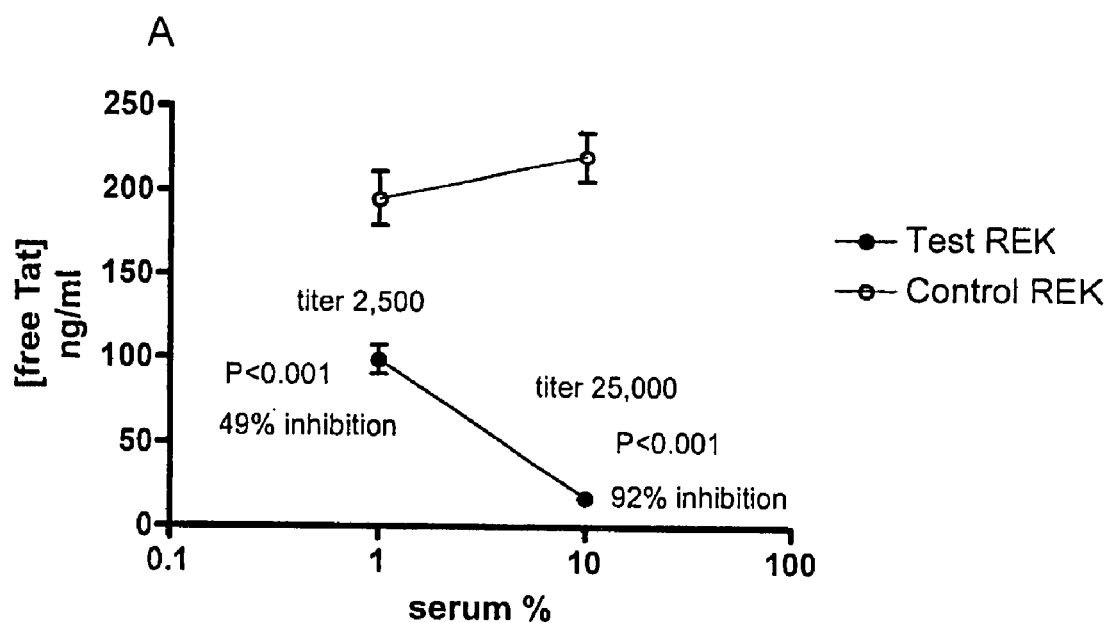
FIG. 7A is a graph demonstrating the % inhibition or reduction of free Tat concentration by use of a medium titer anti-Tat sera (5 mice per group) in the ELISA of Example 4B. The mouse sera titer was 256,000, with 10% dilution having a titer of 25,000 and 1% dilution having a titer of 2,500. Test REK (◇) is the sera of mice immunized with experimental immunogen tested on the REK Tat variant. Control REK (◇, the bolded diamond) is normal mouse serum tested on the REK Tat variant. Immunized mouse sera at 1% dilution showed 49% inhibition of free Tat concentration, while at 10% dilution, the sera showed 92% inhibition, in comparison to the high Tat concentration in the Control.
Figure 7B:
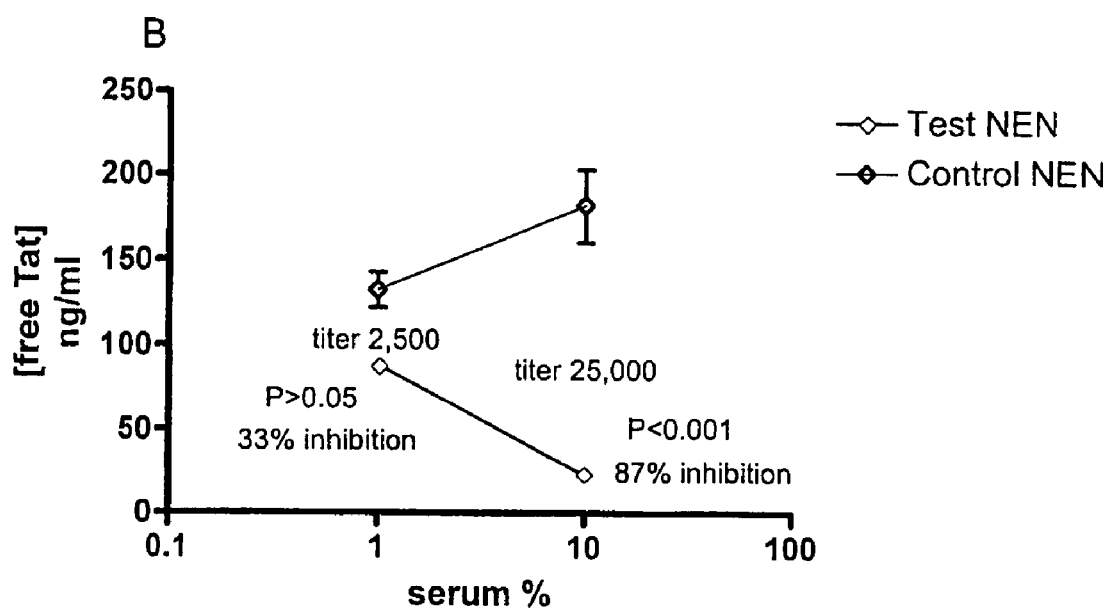
FIG. 7B is a graph demonstrating the % inhibition or reduction of free Tat concentration by use of a medium titer anti-Tat sera (5 mice per group) in the ELISA of Example 4B. The mouse sera antibody titer was 256,000, with 10% dilution having a titer of 25,000 and 1% dilution having a titer of 2,500. Test NEN(◇) is the sera of mice immunized with experimental immunogen tested on the NEN Tat variant. Control NEN (◇, the bolded diamond) is normal mouse serum tested on the NEN variant. Test NEN at 1% dilution showed 33% inhibition of free Tat concentration, while at 10% dilution, it showed 87% inhibition, in comparison to the high Tat concentration in the Control.

FIGS. 7A and 7B demonstrate the % inhibition or reduction of free Tat by the antibodies in the sera. The 10% dilution had a titer of 25,000 and 1% dilution had a titer of 2,500. The sera of mice immunized with experimental immunogen (Test REK) when tested on the REK Tat variant showed 49% inhibition of free Tat concentration at 1% dilution and 92% inhibition at 10% dilution, in comparison to the high Tat concentration in the controls. Similar results were shown by the immunized mouse sera tested on NEN. At 1% dilution, 33% inhibition of free Tat concentration was measured; while at 10% dilution, 87% inhibition was measured, in comparison to the high Tat concentration in the Control. These inhibitions were statistically significant, as shown by the displayed P values on the figures.

Example 5

Titers—Effects of Vaccine Construct, Dose, Frequency and Species

A. Immunizations

Animals were purchased from Harlan Laboratories and acclimated at Molecular Diagnostic Services, Inc., for at least one week before immunization. Both BALBc and C57BL6/BALBc F1 mice were used. Lewis rats were used as indicated. Immunogens prepared as described in Example 1 were taken up in buffered saline and injected IP in mice and rats, and administered subcutaneously in Cynomolgous macaque. Animals were immunized with immunogen at Day 0 and Week 2 (day 14) and serums were obtained at Week 4 (day 28) for titration. Doses/animal are noted in Table 4, along with their anti-Tat titers.

TABLE 4

| Pam3C-capped Immunogen | | |
|---|---|---|
| Species | Dose/animal Mg | 4 week anti-Tat titer GMT |
| Mouse | 1.0 | 120,000* |
| Mouse | 3.0 | 220,000 |
| Mouse | 10.0 | Lethal** |
| Rat | 1.0 | 170,000 |
| Rat | 10.0 | 460,000 |
| Cynomolgous macaque | 10.0 | 900,000 |

*By comparison the Pam2C-capped peptide, at 1.0 mg/mouse in a similar protocol, gave a GMT of 400,000.
**This dose represents 400 mg/kg. No toxicity was observed with 10.0 or 30.0 mg/rat (40.0 and 120.0 mg/kg, respectively) or with 10.0 mg/monkey (5.0 mg/kg). 10.0 mg in a 70 kg human represents 0.14 mg/kg.

B. Results

An optimal dose of 10.0 mg/animal was identified for rats and monkeys. Using comparable doses/animal, titers were greater in monkeys than in rats, and greater in rats than in mice. Toxicity appears related to dose/kg, yet immunogenicity does not appear to be related. The Pam2C- capped immunogen was found to induce higher titers than the Pam3C-capped immunogen.

Example 6

Optimization of Dosage Regimen

A. Immunizations

Animals were purchased from Harlan Laboratories and acclimated at Molecular Diagnostic Services, Inc., for at least one week before immunization. Both BALBc and C57BL6/BALBc F1 mice were used. Pam2C-capped immunogens prepared as described in Example 1 were taken up in buffered saline and injected IP. Mice were immunized with 3 injections of 1.0 mg/mouse Pam2C-capped immunogen with titrations before first boost and 2 weeks after each boost according to Table 5.

Serums were obtained as indicated in Table 5.

TABLE 5

| Prime boost (day/week) | Titer, GMT* (week of bleed) | Titer, GMT (week of bleed) | Titer, GMT (week of bleed) |
|---|---|---|---|
| D0, W2, W4 | 140,000 (2) | 950,000 (4) | 750,000 (6) |
| D0, W3, W6 | 160,000 (3) | 930,000 (5) | 3,300,000 (8) |
| D0, W4, W8 | 70,000 (4) | 400,000 (6) | 3,000,000 (10) |

*GMT geometric mean titer

B. Results

Three consecutive weekly injections provided the highest titers. It is expected based on the data in Table 4 (see Example 5) that this protocol will induce even higher titers in rats and monkeys.

Example 7

GMT for Rat Immunized with Pam3C-capped Peptide

Figure 9:
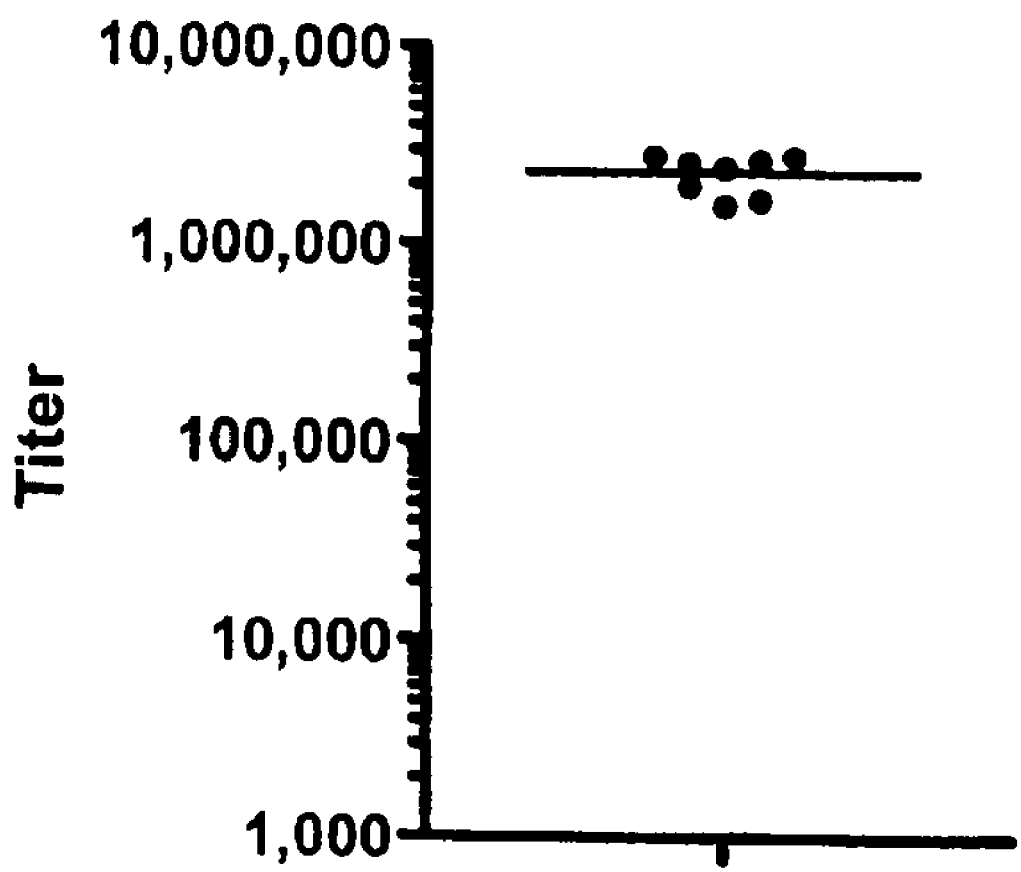
FIG. 9 is a graph showing the titers of antibodies in the serum of a single rat immunized with a mixture of all of the experimental immunogens encompassed by the formula Pam3C-S-S-Q-Y-I-K-A-N-S-K-F-I-G-I-T-E-L -S-V-D-P-(R/K/N/S)-L-(E/D)-P-W-(K/N)-H-P-G-S-amide (SEQ ID NO: 50; Tat amino acid residue 7, 9, and 12 "wobbles") (see Example 1) versus eight full length rTat (AA1-72) variant proteins named by the amino acid residues at wobble positions 7, 9 and 12 (REK, KEK, SEK, NEK, NEN, NDN, KEN, and SEN). Each point represents the GMT on one of the eight variants. The serum showed antibody titers >1,000,000 to all eight Tat Epitope 1 variants. A preferred immunization regimen of prime at day 0, first boost at 3 weeks, second boost at 6 weeks and bleed for titer measurements at 8 weeks was used.

Serum from a rat immunized according to the protocol of Example 6 with a mixture of all of the experimental immunogens encompassed by the formula Pam3C-S-S-Q-Y-I-K-A-N-S-K-F-I-G-I-T-E-L -S-V-D-P-(R/K/N/S)-L-(E/D)-P-W-(K/N)-H-P-G-S-amide (SEQ ID NO: 50; Tat amino acid residue 7, 9, and 12 "wobbles") of Example 1 was examined for anti-Tat antibody titer. FIG. 9 is a graph in which each of the 8 points represents the GMT of antibodies in the serum vs. one Tat variant. The serum showed GMTs>1,000,000.

Example 8

Reduction of Free Tat Levels By Immune Serum

A. Tat Depletion Assay

Classical techniques to measure Tat depletion could not be used due to the lack of a membrane that retained antibody but permitted rTat diffusion. Briefly, this assay employs beads coated with antibody which are exposed to rTat and incubated. The antibody binds the Tat, depending upon the amount of Tat in solution. This assay thus measures how well the antibodies in the serum deplete the quantity of full length recombinant Tat.

Control: Normal rat serum not-immunized with HIV-1 Tat B cell epitopes (10% or 1%) was bound to Protein A beads and washed.

Samples: IgG of 10% and 1% serum of the immunized rat were bound to Protein A beads and washed. Undiluted serum has an anti-Tat titer of 1,000,000, as determined according to the method described in Example 3.

Both the Protein A beads of control and of samples were then incubated at room temperature for 30 minutes with a rTat solution. After centrifugation, the levels of Tat in supernatant were measured with a sandwich ELISA. The free Tat after exposure to 10% or 1% immune serum protein A coated beads was expressed as a percentage of the free Tat after exposure to 10% or 1% normal mouse serum protein A coated beads, respectively.

B. Results

Figure 10:
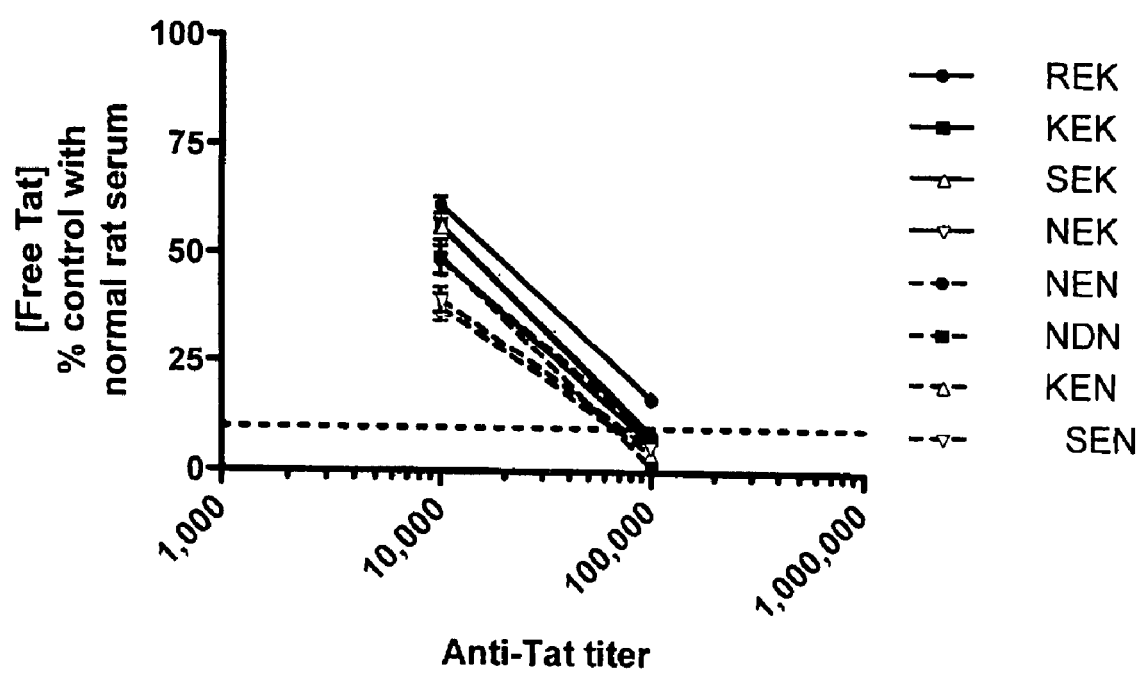
FIG. 10 is a graph showing the results of the Tat depletion assay of Example 8. The concentration of each free full-length rTat variant (named as described above) remaining in solution was measured following incubation with the 1% or 10% rat immune serum (resulting from immunization of a rat with the immunogens of Example 1 bound to Protein A beads. Free Tat was expressed as a percentage of a normal non-immunized rat serum control (free Tat following exposure to 1% or 10% normal rat serum Protein A coated beads). Dotted line is 10% free Tat.

FIG. 10 reflects the results of the assay. 10% of serum was found to bind approximately 90% of Tat in the supernatant. Similarly, 1% of serum was found to bind approximately 50% of Tat in the supernatant.

Example 9

Aqueous Solubilization by Insertion of Polar Charged Sequence within the Linker of the Lipopeptide Cap Immunogens designed with Pam2Cys or Pam3Cys or NAc (Pam2)C as described herein were found to be insoluble in aqueous solvents. To achieve solubility of lipopeptides with all three lipopeptides caps in aqueous solvents, these immunogens were dissolved in dimethylsulphoxide (DMSO) and diluted with phosphate buffered saline to 5-10% DMSO. This yielded an opalescent somewhat turbid solution that was injected into animals.

A Pam2CSKKKKS (SEQ ID NO: 73)- capped lipopeptide was synthesized and was found to have improved solubility, yielding clear solutions. Solubility was best at reduced pH values, with pH 4.0 being optimal and pH 5.0 to 6.0 requiring initial warming and stirring to obtain a clear solution. A clear solution remained after overnight storage at 4° C. Details of the results obtained are reflected in Table 6, below. The Pam2CSKKKKS- (SEQ ID NO: 73) capped lipopeptide was also fully soluble in 25 mg/mL mannitol in water for injection and was readily lyophilized forming a "cake", which was fully soluble in added water for injection.

TABLE 6

| Solution | pH | Appearance | Comments |
|---|---|---|---|
| 2 mg/mL TBS (20 mM Tris, pH 7.4) | 6.5 | Slightly hazy | Partially insoluble |
| 10 mg/mL TBS (20 mM Tris, pH 7.4) | 5.0 | Clear colorless | Soluble with 37° C. incubation |
| 30 mg/mL TBS (20 mM Tris, pH 7.4) | 5.0 | Clear slight straw color | Soluble with 37° C. incubation |
| 2 mg/mL water for injection | 4.0 | Clear colorless | Immediately soluble |
| 30 mg/mL water for injection | 4.0 | Clear slight straw color | Immediately soluble |
| 2 mg/mL injectable saline | 5.0 | Clear colorless | Soluble with 37° C. incubation |
| 30 mg/mL injectable saline | 5.0 | Clear slight straw color | Soluble with 37° C. incubation |

Example 10

GMT for Rats Immunized with Immunogen Containing Charged, Polar Sequence

Three rats per group were immunized with a different dosage per group of a mixture of all of the experimental immunogens encompassed by the formula Pam3C-S-K-K-K-K-S-Q-Y-I-K-A-N-S-K-F-I-G-I-T-E-L -S-V-D-P-(R/K/N/S)-L-(E/D)-P-W-(K/N)-H-P-G-S-amide (SEQ ID NO: 63); Tat amino acid residue 7, 9, and 12 "wobbles") with a polar charged sequence flanked by the linkers of the Pam3C (i.e., -S-K-K-K-K-S-). This immunogen is referred to as "TUTI-K4". Each rat was administered a dose of either 0.1 mg TUTI-K4, or 1 mg TUTI-K4 or 10 mgs TUTI-K4 at day 0. Each rat was boosted with the same dose at week 3. The serum antibody titers for each rat were measured against the full length recombinant Tat (AA 1-72) REK variant protein.

Figure 11:
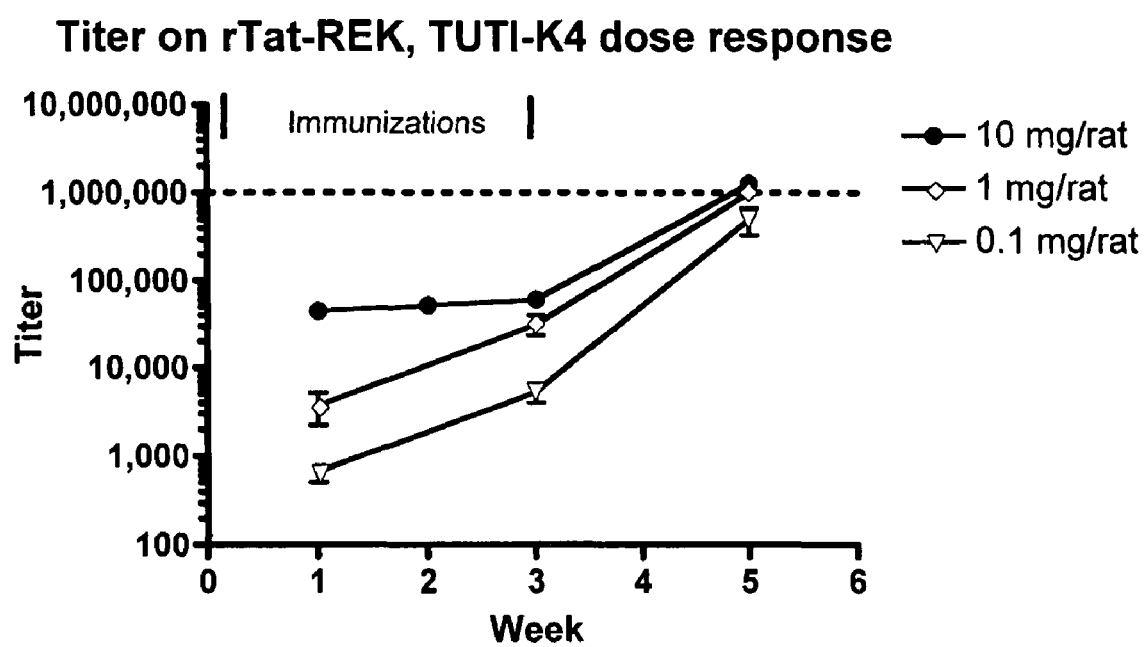
FIG. 11 is a graph showing the titers over time of antibodies in the sera of rats immunized with a mixture of all of the experimental immunogens encompassed by the formula Pam3C-S-K-K-K-K-S-Q-Y-I-K-A-N-S-K-F-I-G-I-T-E-L -S-V-D-P-(R/K/N/S)-L-(E/D)-P-W-(K/N)-H-P-G-S-amide (SEQ ID NO: 63; Tat amino acid residue 7, 9, and 12 "wobbles") with a polar charged sequence flanked by the linkers of the Pam3C (i.e., -S-K-K-K-K-S-) (SEQ ID NO: 64). This immunogen is referred to as "TUTI-K4". Three rats per dose were each administered of either 0.1 mg TUTI-K4 (inverted triangle), or 1 mg TUTI-K4 (diamond) or 10 mgs TUTI-K4 (circle) at day 0 and boosted with the same dose at week 3. The titers are measured against full length rTat (AA1-72) variant protein REK. By week 5, both the 10 mg and 1 mg doses provide GMTs of about 1,000,000 and the 0.1 mg dose provided a GMT of about 500,000. All of these titers are associated with greater than 99% reduction of free Tat levels.

As shown by the graph of FIG. 11, by week 5, all of the doses provided GMTs of about 500,000 (the 0.1 mg dose) or about 1,000,000 (for both the 1 mg and 10 mg doses). All of these titers are associated with greater than 99% reduction of free Tat levels. Despite the more rapid initial titer ascent in the 10 mg group, the rats administered 1 mg/rat appeared to achieve the same titer over 5 weeks. It is anticipated that titers taken after a second boost to be administered at 8 weeks will exceed 3,000,000.

Based upon this data, it is anticipated that this immunogen permits a ten to 100-fold dose reduction in the vaccine amount required to achieve a successful therapeutic titer. For example, doses as low as 0.1 mg/mL or even 0.01 mg/mL are likely to achieve therapeutically effective titers. Such low therapeutically effective doses will provide dramatic and unexpected therapeutic and cost benefits to the patient population worldwide.

Numerous modifications and variations of the embodiments illustrated above are included in this specification and are expected to be obvious to one of skill in the art. Such modifications and alterations to the compositions and processes described herein are believed to be encompassed in the scope of the claims appended hereto. All documents listed or referred to above, including the U.S. provisional application No. 60/837,493, as well as the attached Sequence Listing, are incorporated herein by reference.

What is claimed is:

1. A water-soluble, self-adjuvanting immunogenic composition comprising 16 immunogens, each immunogen comprising:
   (a) a different HIV-1 Tat B cell epitope sequence selected from the group consisting of

| | |
   |---|---|
   | V-D-P-R-L-E-P-W-K-H-P-G-S, | SEQ ID NO: 15 |
   | V-D-P-K-L-E-P-W-K-H-P-G-S, | SEQ ID NO: 16 |
   | V-D-P-N-L-E-P-W-K-H-P-G-S, | SEQ ID NO: 18 |
   | V-D-P-S-L-E-P-W-K-H-P-G-S, | SEQ ID NO: 17 |
   | V-D-P-K-L-E-P-W-N-H-P-G-S, | SEQ ID NO: 21 |
   | V-D-P-N-L-E-P-W-N-H-P-G-S, | SEQ ID NO: 19 |
   | V-D-P-S-L-E-P-W-N-H-P-G-S, | SEQ ID NO: 22 |
   | V-D-P-N-L-D-P-W-N-H-P-G-S, | SEQ ID NO: 20 |
   | V-D-P-R-L-D-P-W-K-H-P-G-S, | SEQ ID NO: 32 |
   | V-D-P-K-L-D-P-W-K-H-P-G-S, | SEQ ID NO: 33 |
   | V-D-P-N-L-D-P-W-K-H-P-G-S, | SEQ ID NO: 34 |
   | V-D-P-S-L-D-P-W-K-H-P-G-S, | SEQ ID NO: 35 |
   | V-D-P-R-L-E-P-W-N-H-P-G-S, | SEQ ID NO: 36 |
   | V-D-P-R-L-D-P-W-N-H-P-G-S, | SEQ ID NO: 37 |
   | V-D-P-K-L-D-P-W-N-H-P-G-S, and | SEQ ID NO: 38 |
   | V-D-P-S-L-D-P-W-N-H-P-G-S. | SEQ ID NO: 39 |

(b) a universal T helper sequence;
   (c) a lipopeptide cap selected from the group consisting of a dipalmitoyl-S-glyceryl-cysteine, a N-acetyl (dipalmitoyl-S-glyceryl cysteine), and a tripalmitoyl-S-glyceryl cysteine; and
   (d) a sequence of charged polar amino acids.

2. The composition according to claim 1, wherein for each immunogen, the lipopeptide cap is linked to the polar sequence, which is linked to the universal T helper sequence, which is linked to the B cell epitope.

3. The composition according to claim 1, further comprising for each immunogen, a linker sequence of from one to ten neutral amino acids, wherein said linker sequence is located between components (a), (b), (c) or (d) of each immunogen.

4. The composition according to claim 3, wherein for each immunogen the sequence of charged polar amino acids is flanked by one or more neutral linker amino acids.

5. The composition according to claim 3, wherein said linker sequence is selected from the group consisting of -S-, -S-S-, -G-, and -G-S-.

6. The composition according to claim 1, wherein said polar sequence comprises a sequence of from 4 to 8 amino acids selected individually from the group consisting of K, E, D, and R, which is optionally flanked by said linker amino acids.

7. The composition according to claim 6, wherein said polar sequence is selected from the group consisting of -K-K-K-K-, -S-K-K-K-K-S-, G-K-K-K-K-G, S-K-K-K-K-K-S, and G-K-K-K-K-K-G (SEQ ID NOs: 65, 64, 70, 69, and 71).

8. The composition according to claim 1, wherein said universal T helper sequence is selected from the group consisting of:
   (a) Q-Y-I-K-A-N-S-K-F-I-G-I-T-E-Xaa SEQ ID NO: 6, wherein said Xaa is absent or L, with an optional amino acid linker;
   (b) Xaa1-K-Xaa2-V-A-A-W-T-L-K-A-A- Xaa3 SEQ ID NO: 46, wherein Xaa1 and Xaa3 are each a D-Alanine and Xaa2 is L-cyclohexylalanine; and
   (c) F-N-N-F-T-V-S-F-W-L-R-V-P-K-V-S-A-S-H-L-E- SEQ ID NO: 23.

9. The composition according to claim 1, wherein each immunogen comprises the lipopeptide cap selected from the group consisting of dipalmitoyl-S-glyceryl-cysteine; N-acetyl-(dipalmitoyl-S-glyceryl cysteine); and tripalmitoyl-S-glyceryl cysteine; the amino acid linker sequence of -S-S- residues, and the universal T cell helper Q-Y-I-K-A-N-S-K-F-I-G-I-T-E-L SEQ ID NO: 47 with an amino acid linker of -S- linking it to the B cell epitope.

10. The composition according to claim 9, wherein a polar amino acid sequence of -K-K-K-K- (SEQ ID NO: 65) is located between the serines of the -S-S- linker sequence.

11. The composition according to claim 1 comprising equimolar amounts of the immunogens.

12. The composition according to claim 4, wherein the polar amino acid sequence is located at a position selected from the group consisting of (a) as part of the carboxy terminus of the lipopeptide cap; (b) at a free amino terminus of the universal T cell helper; (c) at a free amino terminus of said B cell epitope; (d) at the carboxy terminus of the universal T cell helper; (e) at the carboxy terminus of said B cell epitope; (f) interposed between a lysine residue and the universal T cell helper; and (g) interposed between a lysine residue and said B cell epitope.

13. A pharmaceutical composition comprising the self-adjuvanting immunogenic composition of claim 1, and a suitable pharmaceutical carrier or excipient.

14. The composition according to claim 13, wherein said carrier is water for injection and said excipient comprises a tonicity agent.

15. The composition according to claim 13, in lyophilized form.

16. The composition according to claim 13, which comprises a single dosage unit.

* * * * *

SEQUENCE LISTING

```
<160> NUMBER OF SEQ ID NOS: 73

<210> SEQ ID NO 1
<211> LENGTH: 13
<212> TYPE: PRT
<213> ORGANISM: Human immunodeficiency virus type 1
<220> FEATURE:
<221> NAME/KEY: MISC_FEATURE
<222> LOCATION: (4)..(4)
<223> OTHER INFORMATION: can be Arg or Asn or Lys or Ser
<220> FEATURE:
<221> NAME/KEY: MISC_FEATURE
<222> LOCATION: (6)..(6)
<223> OTHER INFORMATION: can be Asp or Glu
<220> FEATURE:
<221> NAME/KEY: MISC_FEATURE
<222> LOCATION: (9)..(9)
<223> OTHER INFORMATION: can be Asn or Lys
<220> FEATURE:
<221> NAME/KEY: MISC_FEATURE
<222> LOCATION: (10)..(10)
<223> OTHER INFORMATION: can be absent or His
<220> FEATURE:
<221> NAME/KEY: MISC_FEATURE
<222> LOCATION: (11)..(11)
<223> OTHER INFORMATION: can be absent or Pro
<220> FEATURE:
<221> NAME/KEY: MISC_FEATURE
<222> LOCATION: (12)..(12)
<223> OTHER INFORMATION: can be absent or Gly
<220> FEATURE:
<221> NAME/KEY: MISC_FEATURE
<222> LOCATION: (13)..(13)
<223> OTHER INFORMATION: can be absent or Ser

<400> SEQUENCE: 1

Val Asp Pro Xaa Leu Xaa Pro Trp Xaa Xaa Xaa Xaa Xaa
1               5                   10

<210> SEQ ID NO 2
<211> LENGTH: 9
<212> TYPE: PRT
<213> ORGANISM: Human immunodeficiency virus type 1
<220> FEATURE:
<221> NAME/KEY: MISC_FEATURE
<222> LOCATION: (4)..(4)
<223> OTHER INFORMATION: can be Arg or Asn or Lys or Ser
<220> FEATURE:
<221> NAME/KEY: MISC_FEATURE
<222> LOCATION: (6)..(6)
<223> OTHER INFORMATION: can be Asp or Glu
<220> FEATURE:
<221> NAME/KEY: MISC_FEATURE
<222> LOCATION: (9)..(9)
<223> OTHER INFORMATION: can be Asn or Lys

<400> SEQUENCE: 2

Val Asp Pro Xaa Leu Xaa Pro Trp Xaa
1               5
```

```
<210> SEQ ID NO 3
<211> LENGTH: 13
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (4)..(4)
<223> OTHER INFORMATION: can be Arg or Asn or Lys or Ser
<220> FEATURE:
<221> NAME/KEY: MISC_FEATURE
<222> LOCATION: (9)..(9)
<223> OTHER INFORMATION: can be Asn or Lys

<400> SEQUENCE: 3

Val Asp Pro Xaa Leu Glu Pro Trp Xaa His Pro Gly Ser
1               5                   10

<210> SEQ ID NO 4
<211> LENGTH: 4
<212> TYPE: PRT
<213> ORGANISM: Human immunodeficiency virus type 1

<400> SEQUENCE: 4

His Pro Gly Ser
1

<210> SEQ ID NO 5
<211> LENGTH: 10
<212> TYPE: PRT
<213> ORGANISM: Human immunodeficiency virus type 1
<220> FEATURE:
<221> NAME/KEY: MISC_FEATURE
<222> LOCATION: (2)..(2)
<223> OTHER INFORMATION: can be Ala or Gly

<400> SEQUENCE: 5

Lys Xaa Leu Gly Ile Ser Tyr Gly Arg Lys
1               5                   10

<210> SEQ ID NO 6
<211> LENGTH: 15
<212> TYPE: PRT
<213> ORGANISM: Clostridium tetani
<220> FEATURE:
<221> NAME/KEY: MISC_FEATURE
<222> LOCATION: (15)..(15)
<223> OTHER INFORMATION: Xaa can be absent or Leu

<400> SEQUENCE: 6

Gln Tyr Ile Lys Ala Asn Ser Lys Phe Ile Gly Ile Thr Glu Xaa
1               5                   10                  15

<210> SEQ ID NO 7
<211> LENGTH: 9
<212> TYPE: PRT
<213> ORGANISM: Human immunodeficiency virus type 1

<400> SEQUENCE: 7

Val Asp Pro Arg Leu Glu Pro Trp Lys
1               5

<210> SEQ ID NO 8
<211> LENGTH: 9
<212> TYPE: PRT
<213> ORGANISM: Human immunodeficiency virus type 1

<400> SEQUENCE: 8
```

Val Asp Pro Lys Leu Glu Pro Trp Lys
1               5

<210> SEQ ID NO 9
<211> LENGTH: 9
<212> TYPE: PRT
<213> ORGANISM: Human immunodeficiency virus type 1

<400> SEQUENCE: 9

Val Asp Pro Ser Leu Glu Pro Trp Lys
1               5

<210> SEQ ID NO 10
<211> LENGTH: 9
<212> TYPE: PRT
<213> ORGANISM: Human immunodeficiency virus type 1

<400> SEQUENCE: 10

Val Asp Pro Asn Leu Glu Pro Trp Lys
1               5

<210> SEQ ID NO 11
<211> LENGTH: 9
<212> TYPE: PRT
<213> ORGANISM: Human immunodeficiency virus type 1

<400> SEQUENCE: 11

Val Asp Pro Asn Leu Glu Pro Trp Asn
1               5

<210> SEQ ID NO 12
<211> LENGTH: 9
<212> TYPE: PRT
<213> ORGANISM: Human immunodeficiency virus type 1

<400> SEQUENCE: 12

Val Asp Pro Asn Leu Asp Pro Trp Asn
1               5

<210> SEQ ID NO 13
<211> LENGTH: 9
<212> TYPE: PRT
<213> ORGANISM: Human immunodeficiency virus type 1

<400> SEQUENCE: 13

Val Asp Pro Lys Leu Glu Pro Trp Asn
1               5

<210> SEQ ID NO 14
<211> LENGTH: 9
<212> TYPE: PRT
<213> ORGANISM: Human immunodeficiency virus type 1

<400> SEQUENCE: 14

Val Asp Pro Ser Leu Glu Pro Trp Asn
1               5

<210> SEQ ID NO 15
<211> LENGTH: 13
<212> TYPE: PRT
<213> ORGANISM: Human immunodeficiency virus type 1

<400> SEQUENCE: 15

Val Asp Pro Arg Leu Glu Pro Trp Lys His Pro Gly Ser
1               5                   10

<210> SEQ ID NO 16
<211> LENGTH: 13
<212> TYPE: PRT
<213> ORGANISM: Human immunodeficiency virus type 1

<400> SEQUENCE: 16

Val Asp Pro Lys Leu Glu Pro Trp Lys His Pro Gly Ser
1               5                   10

<210> SEQ ID NO 17
<211> LENGTH: 13
<212> TYPE: PRT
<213> ORGANISM: Human immunodeficiency virus type 1

<400> SEQUENCE: 17

Val Asp Pro Ser Leu Glu Pro Trp Lys His Pro Gly Ser
1               5                   10

<210> SEQ ID NO 18
<211> LENGTH: 13
<212> TYPE: PRT
<213> ORGANISM: Human immunodeficiency virus type 1

<400> SEQUENCE: 18

Val Asp Pro Asn Leu Glu Pro Trp Lys His Pro Gly Ser
1               5                   10

<210> SEQ ID NO 19
<211> LENGTH: 13
<212> TYPE: PRT
<213> ORGANISM: Human immunodeficiency virus type 1

<400> SEQUENCE: 19

Val Asp Pro Asn Leu Glu Pro Trp Asn His Pro Gly Ser
1               5                   10

<210> SEQ ID NO 20
<211> LENGTH: 13
<212> TYPE: PRT
<213> ORGANISM: Human immunodeficiency virus type 1

<400> SEQUENCE: 20

Val Asp Pro Asn Leu Asp Pro Trp Asn His Pro Gly Ser
1               5                   10

<210> SEQ ID NO 21
<211> LENGTH: 13
<212> TYPE: PRT
<213> ORGANISM: Human immunodeficiency virus type 1

<400> SEQUENCE: 21

Val Asp Pro Lys Leu Glu Pro Trp Asn His Pro Gly Ser
1               5                   10

<210> SEQ ID NO 22
<211> LENGTH: 13
<212> TYPE: PRT
<213> ORGANISM: Human immunodeficiency virus type 1

<400> SEQUENCE: 22

Val Asp Pro Ser Leu Glu Pro Trp Asn His Pro Gly Ser
1               5                   10

<210> SEQ ID NO 23

```
<211> LENGTH: 21
<212> TYPE: PRT
<213> ORGANISM: Clostridium tetani

<400> SEQUENCE: 23

Phe Asn Asn Phe Thr Val Ser Phe Trp Leu Arg Val Pro Lys Val Ser
1               5                   10                  15

Ala Ser His Leu Glu
            20

<210> SEQ ID NO 24
<211> LENGTH: 9
<212> TYPE: PRT
<213> ORGANISM: Human immunodeficiency virus type 1

<400> SEQUENCE: 24

Val Asp Pro Arg Leu Asp Pro Trp Lys
1               5

<210> SEQ ID NO 25
<211> LENGTH: 9
<212> TYPE: PRT
<213> ORGANISM: Human immunodeficiency virus type 1

<400> SEQUENCE: 25

Val Asp Pro Lys Leu Asp Pro Trp Lys
1               5

<210> SEQ ID NO 26
<211> LENGTH: 9
<212> TYPE: PRT
<213> ORGANISM: Human immunodeficiency virus type 1

<400> SEQUENCE: 26

Val Asp Pro Asn Leu Asp Pro Trp Lys
1               5

<210> SEQ ID NO 27
<211> LENGTH: 9
<212> TYPE: PRT
<213> ORGANISM: Human immunodeficiency virus type 1

<400> SEQUENCE: 27

Val Asp Pro Ser Leu Asp Pro Trp Lys
1               5

<210> SEQ ID NO 28
<211> LENGTH: 9
<212> TYPE: PRT
<213> ORGANISM: Human immunodeficiency virus type 1

<400> SEQUENCE: 28

Val Asp Pro Arg Leu Glu Pro Trp Asn
1               5

<210> SEQ ID NO 29
<211> LENGTH: 9
<212> TYPE: PRT
<213> ORGANISM: Human immunodeficiency virus type 1

<400> SEQUENCE: 29

Val Asp Pro Arg Leu Asp Pro Trp Asn
1               5

<210> SEQ ID NO 30
```

```
<211> LENGTH: 9
<212> TYPE: PRT
<213> ORGANISM: Human immunodeficiency virus type 1

<400> SEQUENCE: 30

Val Asp Pro Lys Leu Asp Pro Trp Asn
1               5

<210> SEQ ID NO 31
<211> LENGTH: 9
<212> TYPE: PRT
<213> ORGANISM: Human immunodeficiency virus type 1

<400> SEQUENCE: 31

Val Asp Pro Ser Leu Asp Pro Trp Asn
1               5

<210> SEQ ID NO 32
<211> LENGTH: 13
<212> TYPE: PRT
<213> ORGANISM: Human immunodeficiency virus type 1

<400> SEQUENCE: 32

Val Asp Pro Arg Leu Asp Pro Trp Lys His Pro Gly Ser
1               5                   10

<210> SEQ ID NO 33
<211> LENGTH: 13
<212> TYPE: PRT
<213> ORGANISM: Human immunodeficiency virus type 1

<400> SEQUENCE: 33

Val Asp Pro Lys Leu Asp Pro Trp Lys His Pro Gly Ser
1               5                   10

<210> SEQ ID NO 34
<211> LENGTH: 13
<212> TYPE: PRT
<213> ORGANISM: Human immunodeficiency virus type 1

<400> SEQUENCE: 34

Val Asp Pro Asn Leu Asp Pro Trp Lys His Pro Gly Ser
1               5                   10

<210> SEQ ID NO 35
<211> LENGTH: 13
<212> TYPE: PRT
<213> ORGANISM: Human immunodeficiency virus type 1

<400> SEQUENCE: 35

Val Asp Pro Ser Leu Asp Pro Trp Lys His Pro Gly Ser
1               5                   10

<210> SEQ ID NO 36
<211> LENGTH: 13
<212> TYPE: PRT
<213> ORGANISM: Human immunodeficiency virus type 1

<400> SEQUENCE: 36

Val Asp Pro Arg Leu Glu Pro Trp Asn His Pro Gly Ser
1               5                   10

<210> SEQ ID NO 37
<211> LENGTH: 13
<212> TYPE: PRT
<213> ORGANISM: Human immunodeficiency virus type 1
```

```
<400> SEQUENCE: 37

Val Asp Pro Arg Leu Asp Pro Trp Asn His Pro Gly Ser
1               5                   10

<210> SEQ ID NO 38
<211> LENGTH: 13
<212> TYPE: PRT
<213> ORGANISM: Human immunodeficiency virus type 1

<400> SEQUENCE: 38

Val Asp Pro Lys Leu Asp Pro Trp Asn His Pro Gly Ser
1               5                   10

<210> SEQ ID NO 39
<211> LENGTH: 13
<212> TYPE: PRT
<213> ORGANISM: Human immunodeficiency virus type 1

<400> SEQUENCE: 39

Val Asp Pro Ser Leu Asp Pro Trp Asn His Pro Gly Ser
1               5                   10

<210> SEQ ID NO 40
<211> LENGTH: 20
<212> TYPE: PRT
<213> ORGANISM: Clostridium tetani

<400> SEQUENCE: 40

Ile Asp Lys Ile Ser Asp Val Ser Thr Ile Val Pro Tyr Ile Gly Pro
1               5                   10                  15

Ala Leu Asn Ile
            20

<210> SEQ ID NO 41
<211> LENGTH: 20
<212> TYPE: PRT
<213> ORGANISM: Clostridium tetani

<400> SEQUENCE: 41

Asn Ser Val Asp Asp Ala Leu Ile Asn Ser Thr Lys Ile Tyr Ser Tyr
1               5                   10                  15

Phe Pro Ser Val
            20

<210> SEQ ID NO 42
<211> LENGTH: 17
<212> TYPE: PRT
<213> ORGANISM: Clostridium tetani

<400> SEQUENCE: 42

Pro Gly Ile Asn Gly Lys Ala Ile His Leu Val Asn Asn Glu Ser Ser
1               5                   10                  15

Glu

<210> SEQ ID NO 43
<211> LENGTH: 14
<212> TYPE: PRT
<213> ORGANISM: Clostridium tetani

<400> SEQUENCE: 43

Glx Tyr Ile Lys Ala Asn Ser Lys Phe Ile Gly Ile Thr Glu
1               5                   10
```

-continued

```
<210> SEQ ID NO 44
<211> LENGTH: 21
<212> TYPE: PRT
<213> ORGANISM: Plasmodium falciparum

<400> SEQUENCE: 44

Asp Ile Glu Lys Lys Ile Ala Lys Met Glu Lys Ala Ser Ser Val Phe
1               5                   10                  15

Asn Val Val Asn Ser
            20

<210> SEQ ID NO 45
<211> LENGTH: 16
<212> TYPE: PRT
<213> ORGANISM: Streptococcus mutans

<400> SEQUENCE: 45

Gly Ala Val Asp Ser Ile Leu Gly Gly Val Ala Thr Tyr Gly Ala Ala
1               5                   10                  15

<210> SEQ ID NO 46
<211> LENGTH: 13
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Xaa can be D-Ala or L-Ala
<220> FEATURE:
<221> NAME/KEY: MISC_FEATURE
<222> LOCATION: (3)..(3)
<223> OTHER INFORMATION: Xaa can be L-cyclohexylalanine or phenylalanine
      or tyrosine
<220> FEATURE:
<221> NAME/KEY: MISC_FEATURE
<222> LOCATION: (13)..(13)
<223> OTHER INFORMATION: Xaa can be D-Ala or L-Ala

<400> SEQUENCE: 46

Xaa Lys Xaa Val Ala Ala Trp Thr Leu Lys Ala Ala Xaa
1               5                   10

<210> SEQ ID NO 47
<211> LENGTH: 15
<212> TYPE: PRT
<213> ORGANISM: Clostridium tetani

<400> SEQUENCE: 47

Gln Tyr Ile Lys Ala Asn Ser Lys Phe Ile Gly Ile Thr Glu Leu
1               5                   10                  15

<210> SEQ ID NO 48
<211> LENGTH: 32
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: cys is modified with the lipid,
      dipalmitoyl-S-glyceryl
<220> FEATURE:
<221> NAME/KEY: MISC_FEATURE
<222> LOCATION: (23)..(23)
<223> OTHER INFORMATION: can be Arg or Asn or Lys or Ser
<220> FEATURE:
<221> NAME/KEY: MISC_FEATURE
```

```
<222> LOCATION: (25)..(25)
<223> OTHER INFORMATION: can be Asp or Glu
<220> FEATURE:
<221> NAME/KEY: MISC_FEATURE
<222> LOCATION: (28)..(28)
<223> OTHER INFORMATION: can be Asn or Lys

<400> SEQUENCE: 48

Cys Ser Ser Gln Tyr Ile Lys Ala Asn Ser Lys Phe Ile Gly Ile Thr
1               5                   10                  15

Glu Leu Ser Val Asp Pro Xaa Leu Xaa Pro Trp Xaa His Pro Gly Ser
            20                  25                  30

<210> SEQ ID NO 49
<211> LENGTH: 32
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: cys is a modified N-acetyl-cysteine and is
      further modified with the lipid, dipalmitoyl-S-glyceryl
<220> FEATURE:
<221> NAME/KEY: MISC_FEATURE
<222> LOCATION: (23)..(23)
<223> OTHER INFORMATION: can be Arg or Asn or Lys or Ser
<220> FEATURE:
<221> NAME/KEY: MISC_FEATURE
<222> LOCATION: (25)..(25)
<223> OTHER INFORMATION: can be Asp or Glu
<220> FEATURE:
<221> NAME/KEY: MISC_FEATURE
<222> LOCATION: (28)..(28)
<223> OTHER INFORMATION: can be Asn or Lys

<400> SEQUENCE: 49

Cys Ser Ser Gln Tyr Ile Lys Ala Asn Ser Lys Phe Ile Gly Ile Thr
1               5                   10                  15

Glu Leu Ser Val Asp Pro Xaa Leu Xaa Pro Trp Xaa His Pro Gly Ser
            20                  25                  30

<210> SEQ ID NO 50
<211> LENGTH: 32
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: cys is modified with the lipid,
      tripalmitoyl-S-glyceryl
<220> FEATURE:
<221> NAME/KEY: MISC_FEATURE
<222> LOCATION: (23)..(23)
<223> OTHER INFORMATION: can be Arg or Asn or Lys or Ser
<220> FEATURE:
<221> NAME/KEY: MISC_FEATURE
<222> LOCATION: (25)..(25)
<223> OTHER INFORMATION: can be Asp or Glu
<220> FEATURE:
<221> NAME/KEY: MISC_FEATURE
<222> LOCATION: (28)..(28)
<223> OTHER INFORMATION: can be Asn or Lys

<400> SEQUENCE: 50

Cys Ser Ser Gln Tyr Ile Lys Ala Asn Ser Lys Phe Ile Gly Ile Thr
1               5                   10                  15

Glu Leu Ser Val Asp Pro Xaa Leu Xaa Pro Trp Xaa His Pro Gly Ser
            20                  25                  30
```

```
<210> SEQ ID NO 51
<211> LENGTH: 30
<212> TYPE: PRT
<213> ORGANISM: Artificial
<220> FEATURE:
<223> OTHER INFORMATION: chemically syntheiszed
<220> FEATURE:
<221> NAME/KEY: MISC_FEATURE
<222> LOCATION: (17)..(17)
<223> OTHER INFORMATION: Lys is modified at the epsilon amino group
      with one of these modified lipopeptides, Pam2C-S-S or
      Pam2NAcC-S-S or Pam3C-S-S
<220> FEATURE:
<221> NAME/KEY: MISC_FEATURE
<222> LOCATION: (21)..(21)
<223> OTHER INFORMATION: can be Arg or Asn or Lys or Ser
<220> FEATURE:
<221> NAME/KEY: MISC_FEATURE
<222> LOCATION: (23)..(23)
<223> OTHER INFORMATION: can be Asp or Glu
<220> FEATURE:
<221> NAME/KEY: MISC_FEATURE
<222> LOCATION: (26)..(26)
<223> OTHER INFORMATION: can be Asn or Lys

<400> SEQUENCE: 51

Gln Tyr Ile Lys Ala Asn Ser Lys Phe Ile Gly Ile Thr Glu Leu Ser
1               5                   10                  15

Lys Val Asp Pro Xaa Leu Xaa Pro Trp Xaa His Pro Gly Ser
            20                  25                  30

<210> SEQ ID NO 52
<211> LENGTH: 30
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (20)..(20)
<223> OTHER INFORMATION: can be Arg or Asn or Lys or Ser
<220> FEATURE:
<221> NAME/KEY: MISC_FEATURE
<222> LOCATION: (22)..(22)
<223> OTHER INFORMATION: can be Asn or Glu
<220> FEATURE:
<221> NAME/KEY: MISC_FEATURE
<222> LOCATION: (25)..(25)
<223> OTHER INFORMATION: can be Asn or Lys
<220> FEATURE:
<221> NAME/KEY: MISC_FEATURE
<222> LOCATION: (30)..(30)
<223> OTHER INFORMATION: Lys is modified at the epsilon amino group with
      one of these modified lipopeptides, Pam2C-S-S or Pam2NAcC-S-S or
      Pam3C-S-S

<400> SEQUENCE: 52

Gln Tyr Ile Lys Ala Asn Ser Lys Phe Ile Gly Ile Thr Glu Leu Ser
1               5                   10                  15

Val Asp Pro Xaa Leu Xaa Pro Trp Xaa His Pro Gly Ser Lys
            20                  25                  30

<210> SEQ ID NO 53
<211> LENGTH: 30
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (4)..(4)
<223> OTHER INFORMATION: can be Arg or Asn or Lys or Ser
```

```
<220> FEATURE:
<221> NAME/KEY: MISC_FEATURE
<222> LOCATION: (6)..(6)
<223> OTHER INFORMATION: can be Asp or Glu
<220> FEATURE:
<221> NAME/KEY: MISC_FEATURE
<222> LOCATION: (9)..(9)
<223> OTHER INFORMATION: can be Asn or Lys
<220> FEATURE:
<221> NAME/KEY: MISC_FEATURE
<222> LOCATION: (14)..(14)
<223> OTHER INFORMATION: Lys is modified at the epsilon amino group with
      one of these modified lipopeptides, Pam2C-S-S or Pam2NAcC-S-S or
      Pam3C-S-S

<400> SEQUENCE: 53

Val Asp Pro Xaa Leu Xaa Pro Trp Xaa His Pro Gly Ser Lys Ser Gln
1               5                   10                  15

Tyr Ile Lys Ala Asn Ser Lys Phe Ile Gly Ile Thr Glu Leu
            20                  25                  30

<210> SEQ ID NO 54
<211> LENGTH: 30
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (16)..(16)
<223> OTHER INFORMATION: Lys is modified at the epsilon amino group with
      one of these modified lipopeptides, Pam2C-S-S or Pam2NAcC-S-S or
      Pam3C-S-S
<220> FEATURE:
<221> NAME/KEY: MISC_FEATURE
<222> LOCATION: (21)..(21)
<223> OTHER INFORMATION: can be Arg or Lys or Asn or Ser
<220> FEATURE:
<221> NAME/KEY: MISC_FEATURE
<222> LOCATION: (23)..(23)
<223> OTHER INFORMATION: can be Asp or Glu
<220> FEATURE:
<221> NAME/KEY: MISC_FEATURE
<222> LOCATION: (26)..(26)
<223> OTHER INFORMATION: can be Asn or Lys

<400> SEQUENCE: 54

Gln Tyr Ile Lys Ala Asn Ser Lys Phe Ile Gly Ile Thr Glu Leu Lys
1               5                   10                  15

Ser Val Asp Pro Xaa Leu Xaa Pro Trp Xaa His Pro Gly Ser
            20                  25                  30

<210> SEQ ID NO 55
<211> LENGTH: 14
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (5)..(5)
<223> OTHER INFORMATION: can be Arg or Asn or Lys or Ser
<220> FEATURE:
<221> NAME/KEY: MISC_FEATURE
<222> LOCATION: (7)..(7)
<223> OTHER INFORMATION: can be Asp or Glu
<220> FEATURE:
<221> NAME/KEY: MISC_FEATURE
<222> LOCATION: (10)..(10)
<223> OTHER INFORMATION: can be Asn or Lys

<400> SEQUENCE: 55

Ser Val Asp Pro Xaa Leu Xaa Pro Trp Xaa His Pro Gly Ser
```

```
<210> SEQ ID NO 56
<211> LENGTH: 14
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Lys is modified  with one of these modified
      lipopeptides, Pam2C-S-S or Pam2NAcC-S-S or Pam3C-S-S
<220> FEATURE:
<221> NAME/KEY: MISC_FEATURE
<222> LOCATION: (5)..(5)
<223> OTHER INFORMATION: can be Arg or Asn or Lys or Ser
<220> FEATURE:
<221> NAME/KEY: MISC_FEATURE
<222> LOCATION: (7)..(7)
<223> OTHER INFORMATION: can be Asp or Glu
<220> FEATURE:
<221> NAME/KEY: MISC_FEATURE
<222> LOCATION: (10)..(10)
<223> OTHER INFORMATION: can be Asn or Lys

<400> SEQUENCE: 56

Lys Val Asp Pro Xaa Leu Xaa Pro Trp Xaa His Pro Gly Ser
1               5                   10

<210> SEQ ID NO 57
<211> LENGTH: 15
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (4)..(4)
<223> OTHER INFORMATION: can be Arg or Asn or Lys or Ser
<220> FEATURE:
<221> NAME/KEY: MISC_FEATURE
<222> LOCATION: (6)..(6)
<223> OTHER INFORMATION: can be Asn or Glu
<220> FEATURE:
<221> NAME/KEY: MISC_FEATURE
<222> LOCATION: (9)..(9)
<223> OTHER INFORMATION: can be Asn or Lys
<220> FEATURE:
<221> NAME/KEY: MISC_FEATURE
<222> LOCATION: (14)..(14)
<223> OTHER INFORMATION: Lys is modified with one of these modified
      lipopeptides, Pam2C-S-S or Pam2NAcC-S-S or Pam3C-S-S

<400> SEQUENCE: 57

Val Asp Pro Xaa Leu Xaa Pro Trp Xaa His Pro Gly Ser Lys Ser
1               5                   10                  15

<210> SEQ ID NO 58
<211> LENGTH: 29
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (20)..(20)
<223> OTHER INFORMATION: can be Arg or Asn or Lys or Ser
<220> FEATURE:
<221> NAME/KEY: MISC_FEATURE
<222> LOCATION: (22)..(22)
<223> OTHER INFORMATION: can be Asp or Glu
<220> FEATURE:
<221> NAME/KEY: MISC_FEATURE
<222> LOCATION: (25)..(25)
```

```
<223> OTHER INFORMATION: can be Asn or Lys

<400> SEQUENCE: 58

Gln Tyr Ile Lys Ala Asn Ser Lys Phe Ile Gly Ile Thr Glu Leu Ser
1               5                   10                  15

Val Asp Pro Xaa Leu Xaa Pro Trp Xaa His Pro Gly Ser
            20                  25

<210> SEQ ID NO 59
<211> LENGTH: 32
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: lys is modified with the lipid,
      dipalmitoyl-S-glyceryl
<220> FEATURE:
<221> NAME/KEY: MISC_FEATURE
<222> LOCATION: (23)..(23)
<223> OTHER INFORMATION: can be Arg or Asn or Lys or Ser
<220> FEATURE:
<221> NAME/KEY: MISC_FEATURE
<222> LOCATION: (25)..(25)
<223> OTHER INFORMATION: can be Asp or Glu
<220> FEATURE:
<221> NAME/KEY: MISC_FEATURE
<222> LOCATION: (28)..(28)
<223> OTHER INFORMATION: can be Asn or Lys

<400> SEQUENCE: 59

Lys Ser Ser Gln Tyr Ile Lys Ala Asn Ser Lys Phe Ile Gly Ile Thr
1               5                   10                  15

Glu Leu Ser Val Asp Pro Xaa Leu Xaa Pro Trp Xaa His Pro Gly Ser
            20                  25                  30

<210> SEQ ID NO 60
<211> LENGTH: 36
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: cys is modified with the lipid,
      dipalmitoyl-S-glyceryl
<220> FEATURE:
<221> NAME/KEY: MISC_FEATURE
<222> LOCATION: (27)..(27)
<223> OTHER INFORMATION: can be Arg or Asn or Lys or Ser
<220> FEATURE:
<221> NAME/KEY: MISC_FEATURE
<222> LOCATION: (29)..(29)
<223> OTHER INFORMATION: can be Asp or Glu
<220> FEATURE:
<221> NAME/KEY: MISC_FEATURE
<222> LOCATION: (32)..(32)
<223> OTHER INFORMATION: can be Asn or Lys

<400> SEQUENCE: 60

Cys Ser Lys Lys Lys Lys Ser Gln Tyr Ile Lys Ala Asn Ser Lys Phe
1               5                   10                  15

Ile Gly Ile Thr Glu Leu Ser Val Asp Pro Xaa Leu Xaa Pro Trp Xaa
            20                  25                  30

His Pro Gly Ser
            35
```

```
<210> SEQ ID NO 61
<211> LENGTH: 37
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: cys is modified with the lipid,
      dipalmitoyl-S-glyceryl
<220> FEATURE:
<221> NAME/KEY: MISC_FEATURE
<222> LOCATION: (28)..(28)
<223> OTHER INFORMATION: can be Arg or Asn or Lys or Ser
<220> FEATURE:
<221> NAME/KEY: MISC_FEATURE
<222> LOCATION: (30)..(30)
<223> OTHER INFORMATION: can be Asp or Glu
<220> FEATURE:
<221> NAME/KEY: MISC_FEATURE
<222> LOCATION: (33)..(33)
<223> OTHER INFORMATION: can be Asn or Lys

<400> SEQUENCE: 61

Cys Ser Ser Gln Tyr Ile Lys Ala Asn Ser Lys Phe Ile Gly Ile Thr
1               5                   10                  15

Glu Leu Ser Lys Lys Lys Lys Ser Val Asp Pro Xaa Leu Xaa Pro Trp
            20                  25                  30

Xaa His Pro Gly Ser
        35

<210> SEQ ID NO 62
<211> LENGTH: 41
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: cys is modified with the lipid,
      dipalmitoyl-S-glyceryl
<220> FEATURE:
<221> NAME/KEY: MISC_FEATURE
<222> LOCATION: (32)..(32)
<223> OTHER INFORMATION: can be Arg or Asn or Lys or Ser
<220> FEATURE:
<221> NAME/KEY: MISC_FEATURE
<222> LOCATION: (34)..(34)
<223> OTHER INFORMATION: can be Asp or Glu
<220> FEATURE:
<221> NAME/KEY: MISC_FEATURE
<222> LOCATION: (37)..(37)
<223> OTHER INFORMATION: can be Asn or Lys

<400> SEQUENCE: 62

Cys Ser Lys Lys Lys Lys Ser Gln Tyr Ile Lys Ala Asn Ser Lys Phe
1               5                   10                  15

Ile Gly Ile Thr Glu Leu Ser Lys Lys Lys Ser Val Asp Pro Xaa
            20                  25                  30

Leu Xaa Pro Trp Xaa His Pro Gly Ser
        35                  40

<210> SEQ ID NO 63
<211> LENGTH: 36
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
```

```
<222> LOCATION: (1)..(1)
<223> OTHER INFORMATION: cys is modified with the lipid,
      tripalmitoyl-S-glyceryl
<220> FEATURE:
<221> NAME/KEY: MISC_FEATURE
<222> LOCATION: (27)..(27)
<223> OTHER INFORMATION: can be Arg or Asn or Lys or Ser
<220> FEATURE:
<221> NAME/KEY: MISC_FEATURE
<222> LOCATION: (29)..(29)
<223> OTHER INFORMATION: can be Asp or Glu
<220> FEATURE:
<221> NAME/KEY: MISC_FEATURE
<222> LOCATION: (32)..(32)
<223> OTHER INFORMATION: can be Asn or Lys

<400> SEQUENCE: 63

Cys Ser Lys Lys Lys Ser Gln Tyr Ile Lys Ala Asn Ser Lys Phe
1               5                   10                  15

Ile Gly Ile Thr Glu Leu Ser Val Asp Pro Xaa Leu Xaa Pro Trp Xaa
            20                  25                  30

His Pro Gly Ser
        35

<210> SEQ ID NO 64
<211> LENGTH: 6
<212> TYPE: PRT
<213> ORGANISM: Artificial
<220> FEATURE:
<223> OTHER INFORMATION: linker sequence

<400> SEQUENCE: 64

Ser Lys Lys Lys Lys Ser
1               5

<210> SEQ ID NO 65
<211> LENGTH: 4
<212> TYPE: PRT
<213> ORGANISM: Artificial
<220> FEATURE:
<223> OTHER INFORMATION: linker sequence

<400> SEQUENCE: 65

Lys Lys Lys Lys
1

<210> SEQ ID NO 66
<211> LENGTH: 6
<212> TYPE: PRT
<213> ORGANISM: Artificial
<220> FEATURE:
<223> OTHER INFORMATION: linker sequence

<400> SEQUENCE: 66

Lys Lys Lys Lys Lys Lys
1               5

<210> SEQ ID NO 67
<211> LENGTH: 4
<212> TYPE: PRT
<213> ORGANISM: Artificial
<220> FEATURE:
<223> OTHER INFORMATION: linker sequence

<400> SEQUENCE: 67

Lys Glu Lys Glu
1
```

```
<210> SEQ ID NO 68
<211> LENGTH: 4
<212> TYPE: PRT
<213> ORGANISM: Artificial
<220> FEATURE:
<223> OTHER INFORMATION: linker sequence

<400> SEQUENCE: 68

Glu Glu Glu Glu
1

<210> SEQ ID NO 69
<211> LENGTH: 8
<212> TYPE: PRT
<213> ORGANISM: Artificial
<220> FEATURE:
<223> OTHER INFORMATION: linker sequence

<400> SEQUENCE: 69

Ser Lys Lys Lys Lys Lys Lys Ser
1               5

<210> SEQ ID NO 70
<211> LENGTH: 6
<212> TYPE: PRT
<213> ORGANISM: Artificial
<220> FEATURE:
<223> OTHER INFORMATION: linker sequence

<400> SEQUENCE: 70

Gly Lys Lys Lys Lys Gly
1               5

<210> SEQ ID NO 71
<211> LENGTH: 8
<212> TYPE: PRT
<213> ORGANISM: Artificial
<220> FEATURE:
<223> OTHER INFORMATION: linker sequence

<400> SEQUENCE: 71

Gly Lys Lys Lys Lys Lys Lys Gly
1               5

<210> SEQ ID NO 72
<211> LENGTH: 6
<212> TYPE: PRT
<213> ORGANISM: Artificial
<220> FEATURE:
<223> OTHER INFORMATION: linker sequence

<400> SEQUENCE: 72

Ser Lys Glu Lys Glu Ser
1               5

<210> SEQ ID NO 73
<211> LENGTH: 7
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: cys is modified with the lipid,
      dipalmitoyl-S-glyceryl
```

-continued

```
<400> SEQUENCE: 73

Cys Ser Lys Lys Lys Lys Ser
1               5
```